United States Patent
Srinivasan et al.

(10) Patent No.: US 11,951,105 B2
(45) Date of Patent: *Apr. 9, 2024

(54) METHODS OF TREATING PSYCHIATRIC DISORDERS IN OBESE PATIENTS WITH BREXPIPRAZOLE

(71) Applicant: Lake O'Hara LLC, Corona Del Mar, CA (US)

(72) Inventors: Sundar Srinivasan, Corona Del Mar, CA (US); Christina Chow Wallen, Seattle, WA (US)

(73) Assignee: LAKE O'HARA LLC, Corona Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/575,316

(22) Filed: Jan. 13, 2022

(65) Prior Publication Data
US 2022/0378781 A1   Dec. 1, 2022

Related U.S. Application Data

(63) Continuation of application No. 17/139,627, filed on Dec. 31, 2020, now Pat. No. 11,229,644.

(51) Int. Cl.
*A61K 31/496* (2006.01)
*A61P 25/18* (2006.01)
*A61P 25/24* (2006.01)

(52) U.S. Cl.
CPC ............ *A61K 31/496* (2013.01); *A61P 25/18* (2018.01); *A61P 25/24* (2018.01)

(58) Field of Classification Search
CPC ........ A61K 31/192; A61K 45/06; A61K 9/00; A61K 47/14
USPC .................................................... 514/253.07
See application file for complete search history.

(56) References Cited

U.S. PATENT DOCUMENTS

| | | | |
|---|---|---|---|
| 7,888,362 B2* | 2/2011 | Yamashita | A61P 25/18 514/253.05 |
| 11,229,644 B1 | 1/2022 | Srinivasan et al. | |
| 2014/0378447 A1 | 12/2014 | Okano et al. | |
| 2015/0045356 A1* | 2/2015 | Yamashita | A61P 25/24 544/295 |
| 2015/0087655 A1* | 3/2015 | Yamashita | A61P 25/22 514/253.07 |
| 2015/0093442 A1* | 4/2015 | Kaneko | A61P 25/00 514/253.07 |
| 2015/0272946 A1* | 10/2015 | Sato | A61K 31/496 514/253.07 |
| 2017/0100395 A1* | 4/2017 | Hirose | A61K 31/165 |
| 2017/0145001 A1* | 5/2017 | Lee | C07D 409/12 |
| 2018/0036267 A1* | 2/2018 | Tsai | A61K 47/22 |
| 2022/0202810 A1 | 6/2022 | Srinivasan et al. | |

FOREIGN PATENT DOCUMENTS

| | | | |
|---|---|---|---|
| WO | 2009128537 | * | 10/2009 |
| WO | WO-2009128537 A1 | | 10/2009 |
| WO | 2017106641 | * | 6/2017 |
| WO | WO-2017106641 A1 | | 6/2017 |
| WO | 2017120012 | * | 7/2017 |
| WO | WO-2017120012 A1 | | 7/2017 |
| WO | WO-2020018136 A1 | | 1/2020 |
| WO | WO-2020132522 A1 | | 6/2020 |
| WO | WO-2022146462 A1 | | 7/2022 |
| WO | WO-2023141634 A2 | | 7/2023 |

OTHER PUBLICATIONS

Ishigooka et al., The Journal of clinical pharmacology, (2018), 58(1), 74-80.*
Garnock et al., CNS drugs (2016), vol. 30, pp. 335-342.*
Brown et al., Journal of Affective disorders, vol. 249, (2019), pp. 315-318.*
U.S. Appl. No. 17/139,627, filed Dec. 31, 2020, 11,229,644, Jan. 25, 2022, Registered.
U.S. Appl. No. 17/139,690, filed Dec. 31, 2020, Pending.
"Brexpiprazole", Drug Bank Accession No. DB09128, available as of Oct. 28, 2020 at https://web.archive.org/web/20201026193937/https://go.drugbank.com/drugs/DB09128, 8 pages.
Barras and Legg, "A. Drug dosing in obese adults". Australian Prescriber (Oct. 2017); 40(5): 189-193.
Brown, et al., "A pilot study of brexpiprazole for bipolar depression". Journal of Affective Disorders (Apr. 15, 2019); 249: 315-318.
Bruno, et al., "Impact of Obesity on Brexpiprazole Pharmacokinetics: Proposal for Improved Initiation of Treatment". J Clin Pharmacol . (Aug. 2, 2021); 00(0): 1-11. Epub ahead of print. PMID: 34339048.
Center for Drug Evaluation and Research, Clinical Pharmacology and Biopharmaceutics Review(s), NDA Application No. 205,422/0000, REXULTI (Brexpiprazole), Immediate Release Tablet, Dosage Strength (mg)—0.25, 0.5, 1, 2, 3, 4; Sponsor—Otsuka, Submission Date—Jul. 11, 2014, 187 pages.
Centorrino, et al., "Aripiprazole: Initial Clinical Experience with 142 Hospitalized Psychiatric Patients". Journal of Psychiatric Practice (Jul. 2005); 11(4): 241-247.
Co-pending U.S. Appl. No. 17/139,627, filed Dec. 31, 2020.
Elmokadem, et al., "Brexpiprazole Pharmacokinetics in CYP2D6 Poor Metabolizers: Using Physiologically Based Pharmacokinetic Modeling to Optimize Time to Effective Concentrations". J Clin Pharmacol. (Jul. 30, 2021); 00(0): 1-10. Epub ahead of print. PMID: 34328221.

(Continued)

*Primary Examiner* — Niloofar Rahmani
(74) *Attorney, Agent, or Firm* — COOLEY LLP

(57) ABSTRACT

The present disclosure relates to methods of initiating brexpiprazole treating in patients with schizophrenia or major depressive disorder. The present disclosure further relates to modified dosing regimens for obese patients and/or patients that are CYP2D6 poor metabolizers. In embodiments, the modified dosing regimens administers double the daily dose while initiating treatment.

17 Claims, 15 Drawing Sheets

(56) References Cited

OTHER PUBLICATIONS

Garnock-Jones, K.P., "Brexpiprazole: a review in schizophrenia". CNS Drugs (Apr. 1, 2016); 30(4): 335-342.

Hanley, et al., "Effect of Obesity on the Pharmacokinetics of Drugs in Humans", Clinical Pharmacokinetics (2010); 49(2): 71-87.

Hiemke, et al., "Consensus Guidelines for Therapeutic Drug Monitoring in Neuropsychopharmacology: Update 2017." Pharmacopsychiatry (Jan. 2018); 51(01/02): 9-62. Epub Sep. 14, 2017.

Ishigooka, et al., "Pharmacokinetics and Safety of Brexpiprazole Following Multiple-Dose Administration to Japanese Patients With Schizophrenia". The Journal of Clinical Pharmacology (Jan. 2018); 58(1): 74-80.

Laederach-Hofmann, et al., "Links between body mass index, total body fat, cholesterol, high-density lipoprotein, and insulin sensitivity in patients with obesity related to depression, anger, and anxiety", Int J Eat Disord (2002); 32: 58-71. Epub May 14, 2002.

May, et al., "Modern pharmacological treatment of obese patients." Therapeutic Advances in Endocrinology and Metabolism (2020); vol. 11, p. 1-19.

PCT/US2021/016329, International Search Report and Written Opinion dated Apr. 16, 2021, 18 pages.

REXULTI (Brexpiprazole) Tablets, Center for Drug Evaluation and Research, Clinical and Biopharmaceutics Review, NDA Application No. 205.422/0000, Approval Date: Jul. 10, 2015, pages renumbered by Examiner, 189 pages.

REXULTI® (brexpiprazole) Highlights of Prescribing Information / label / package insert, Revised: Mar. 2020 (Mar. 2020), Initial U.S. Approval: 2015, Dosage Forms and Strengths—Tablets: 0.25 mg, 0.5 mg, 1 mg, 2 mg, 3 mg, and 4 mg, Manufactured by Otsuka Pharmaceutical Co., Ltd., Tokyo 101-8535, Japan, Reference ID: 4626222, 29 pages.

Cunha, J. P., "REXULTI", RxList (Dec. 6, 2021) [online] https://web.archive.org/web/20211206085842/https://www.rxlist.com/rexulti-drug.htm#description (Access Date: Aug. 9, 2023); 20 pages.

Farchione, T. R., "NDA 205422", Clinical Pharmacology and Biopharmaceutics Review, Center For Drug Evaluation And Research (2015); 238 pages.

International Preliminary Report on Patentability for International Application No. PCT/US2021/016329 dated Jul. 13, 2023, 13 pages.

International Search Report and Written Opinion for PCT Application No. PCT/US2023/061104 dated Jul. 27, 2023, 17 pages.

Invitation to Pay Fee for International Application No. PCT/US2023/061104 dated Apr. 19, 2023, 3 pages.

REXULTI® (brexpiprazole) Highlights of Prescribing Information / label / package insert, Revised: Dec. 2021 (Dec. 2021), Initial U.S. Approval: 2015, Dosage Forms and Strengths—Tablets: 0.25 mg, 0.5 mg, 1 mg, 2 mg, 3 mg, and 4 mg, Manufactured by Otsuka Pharmaceutical Co., Ltd., Tokyo 101-8535, Japan, 33 pages.

U.S. Appl. No. 17/139,627: Declaration of Dr. David J. Greenblatt with Appendix A; signed Nov. 11, 2021; 16 pages.

U.S. Appl. No. 17/139,627: Declaration of Dr. Thomas A. Posever, signed Nov. 10, 2021; 8 pages.

U.S. Appl. No. 17/139,690: Declaration of Dr. David J. Greenblatt; signed Nov. 12, 2021; 12 pages.

U.S. Appl. No. 17/139,690: Declaration of Dr. David J. Greenblatt; signed Jul. 19, 2021; 16 pages.

U.S. Appl. No. 17/139,690: Declaration of Dr. Thomas A. Posever, signed Nov. 15, 2021; 9 pages.

\* cited by examiner

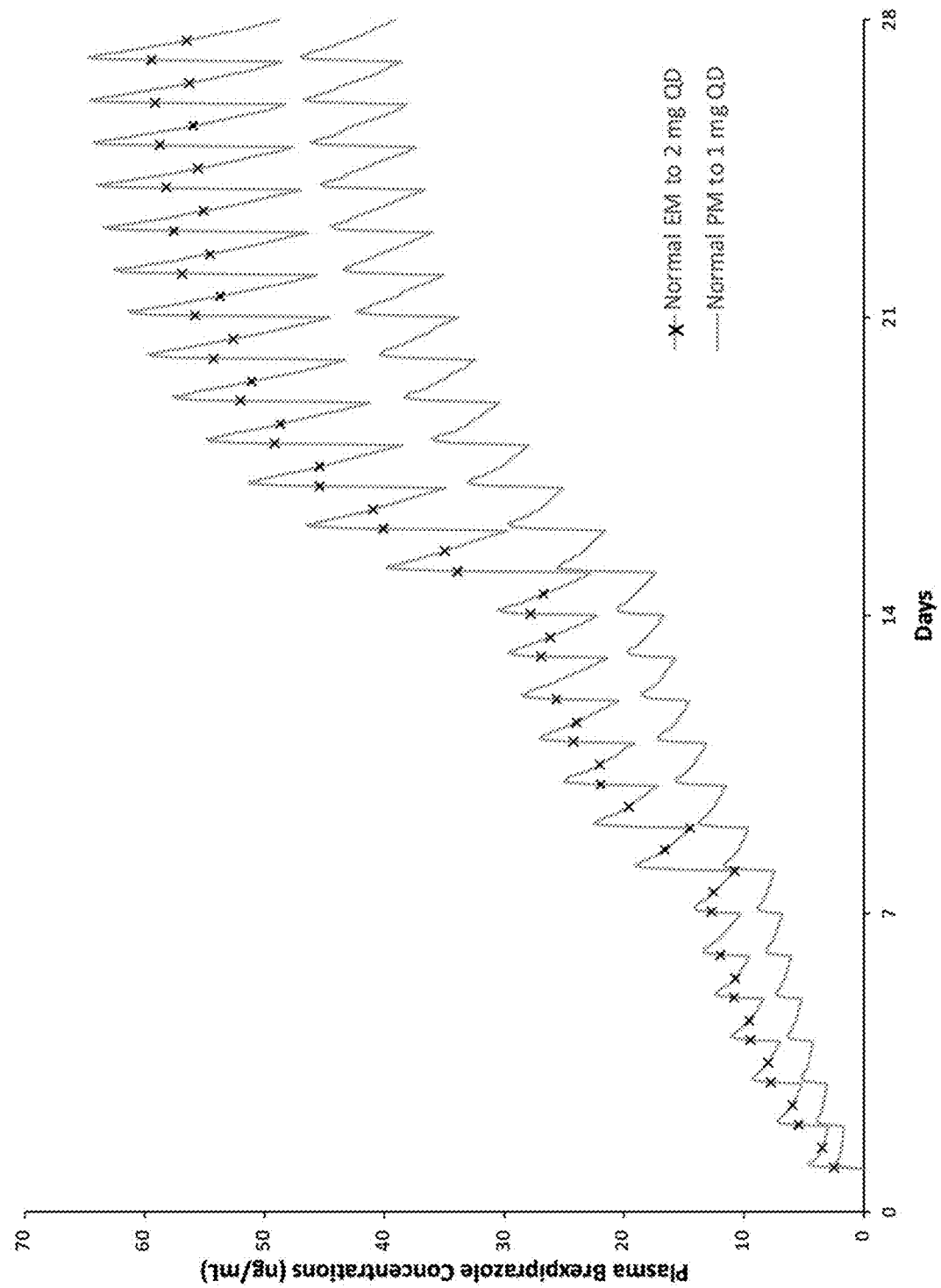

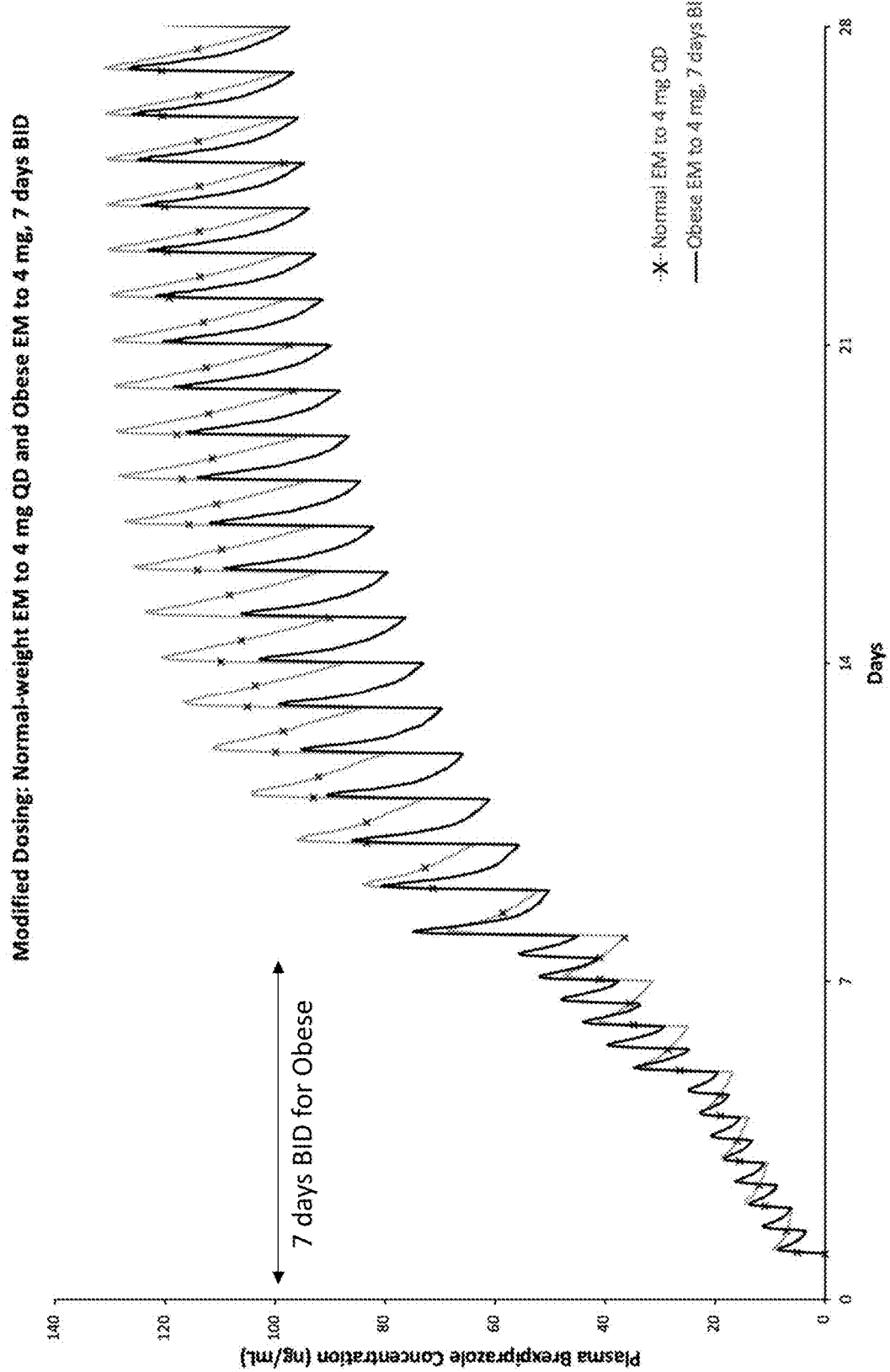

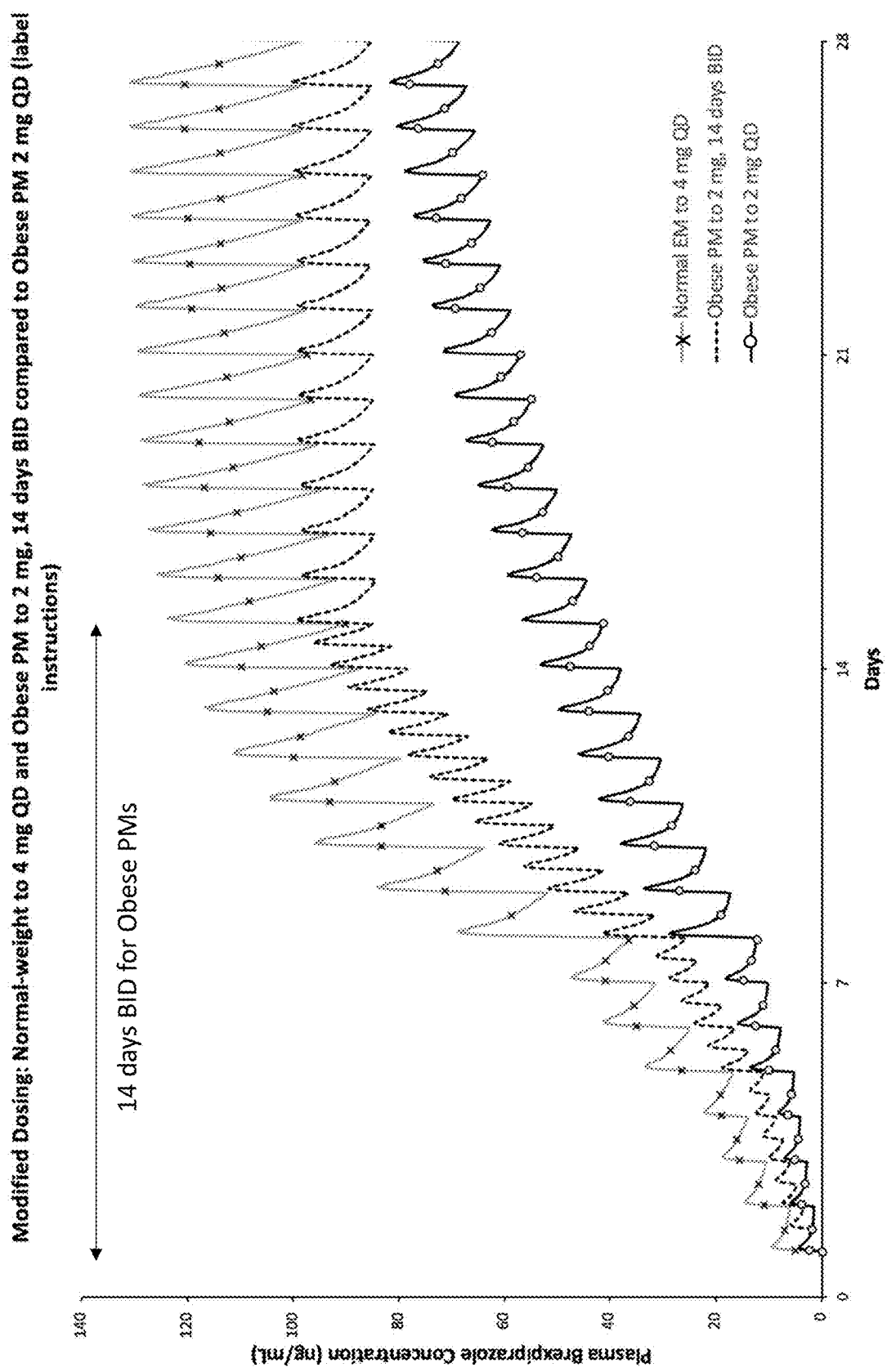

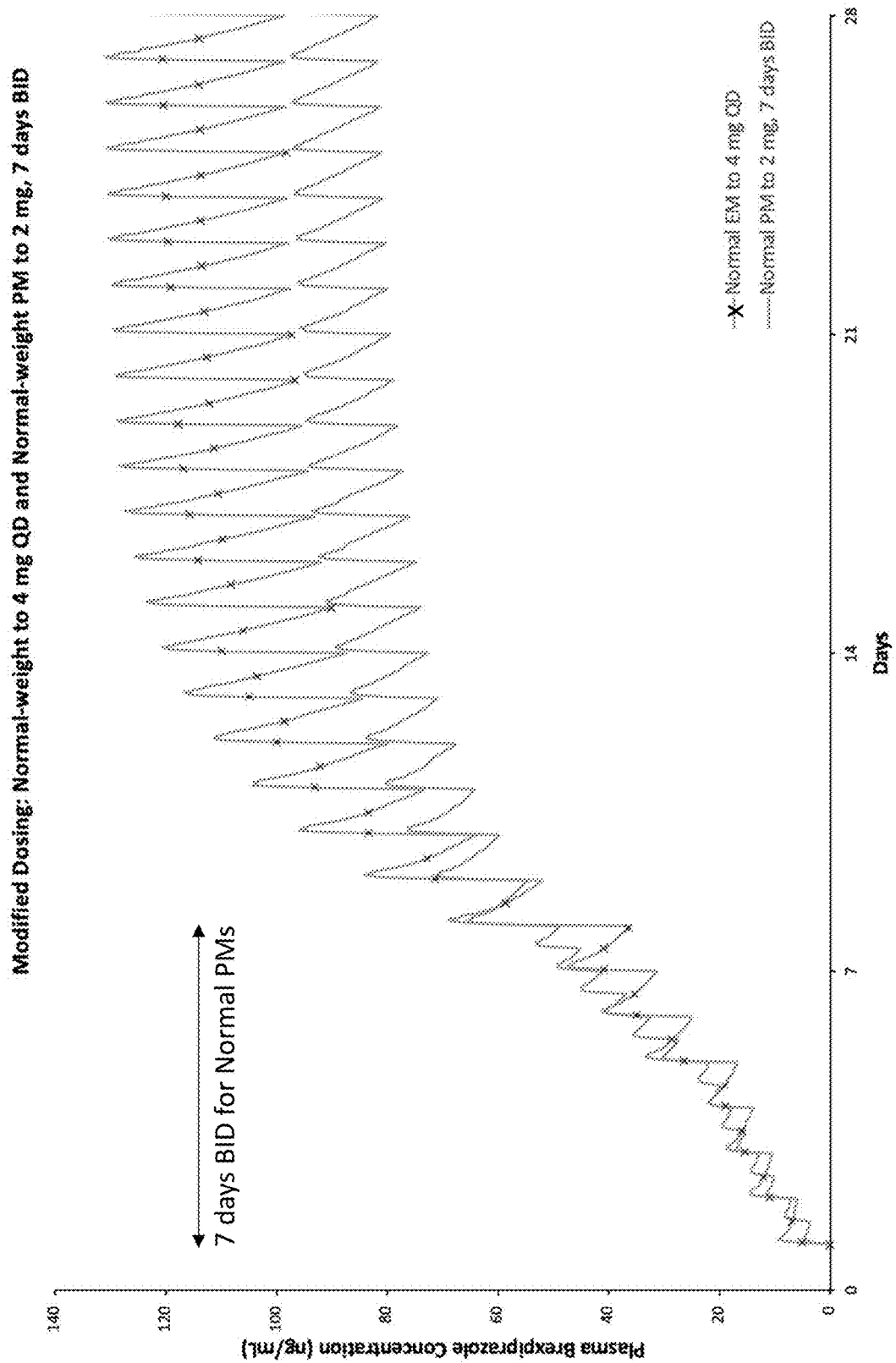

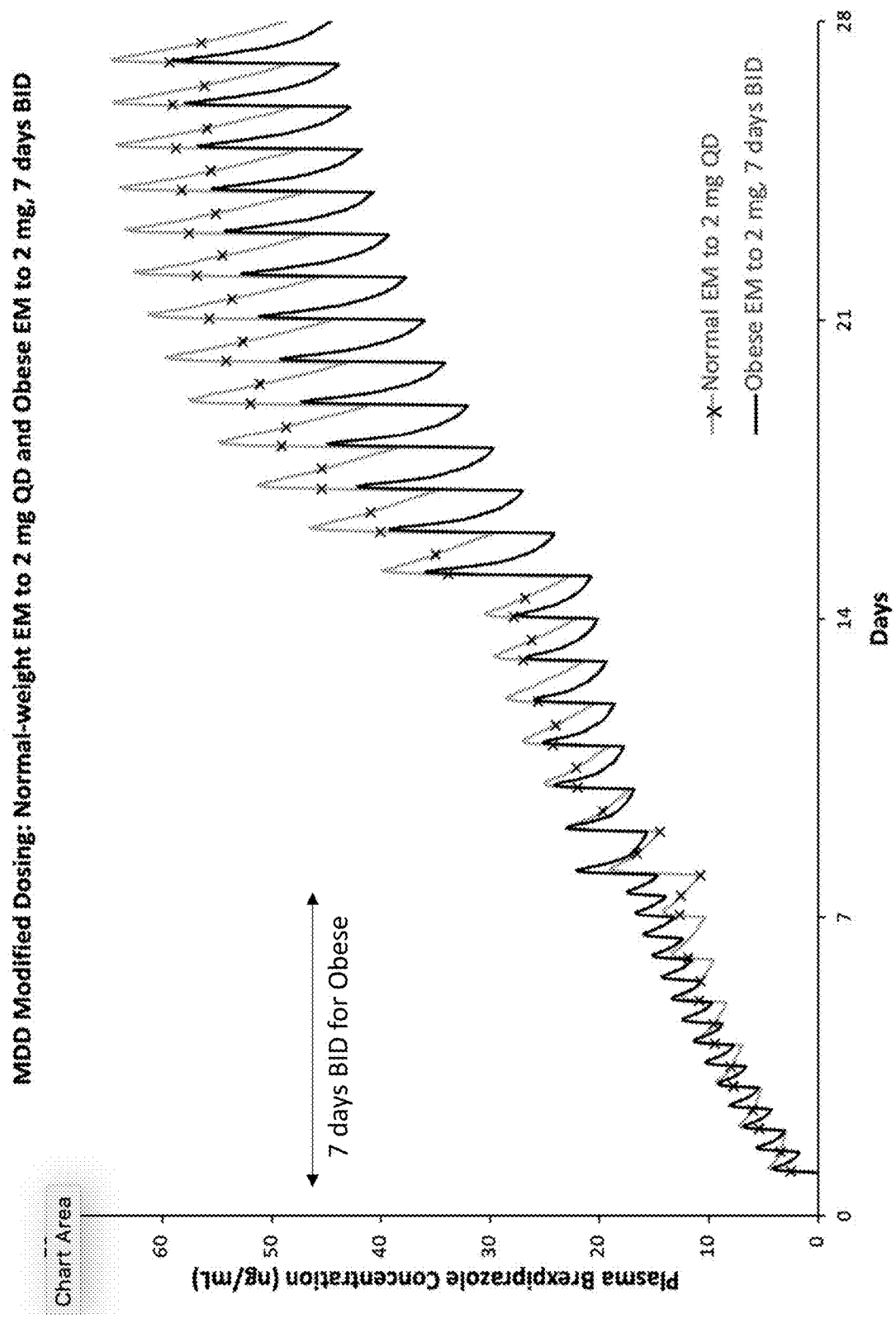

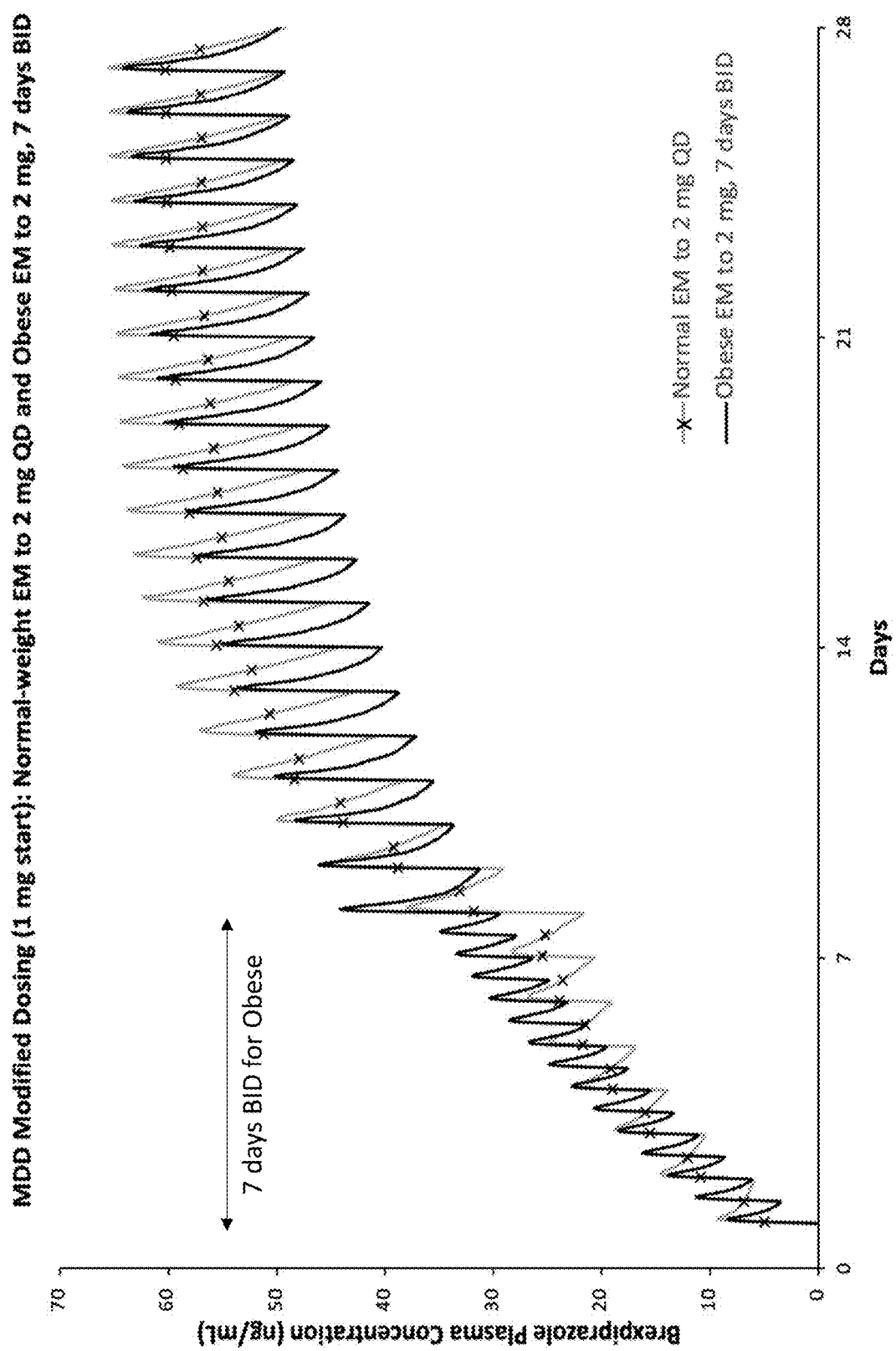

METHODS OF TREATING PSYCHIATRIC DISORDERS IN OBESE PATIENTS WITH BREXPIPRAZOLE

CROSS-REFERENCE TO RELATED APPLICATION

The present Application is a continuation of U.S. application Ser. No. 17/139,627, filed Dec. 31, 2020, the disclosure of which is incorporated by reference herein in their entireties for all purposes.

BACKGROUND

Brexpiprazole, also called REXULTI®, is an atypical antipsychotic used for treating major depressive disorder and schizophrenia. The mechanism of action of brexpiprazole in the treatment of major depressive disorder (MDD) and schizophrenia is unknown. However, the efficacy of brexpiprazole may result from partial agonist activity at serotonin $5\text{-}HT_{1A}$ and dopamine $D_2$ receptors and antagonist activity at serotonin $5\text{-}HT_{2A}$ receptors.

The brexpiprazole (REXULTI®) Food and Drug Administration (FDA) label revised in March 2020 reflects the state-of-the art regarding the appropriate dosing for patients in need of brexpiprazole, and provides instructions for a brexpiprazole starting dose, recommended dose, and maximum dose with a titration timeline based on a patient's clinical response and tolerability. The FDA label also provides instructions to administer half of the usual dose to patients that are CYP2D6 poor metabolizers.

An ideal dosage regimen for brexpiprazole enables psychiatric patients to reach therapeutic levels of brexpiprazole as quickly as possible while avoiding side effects from brexpiprazole. One serious side effect of administering too much brexpiprazole is akathisia, a movement and mental distress disorder which is a state of agitation, distress, and restlessness. Akathisia rates in brexpiprazole patients have been shown to be dose-dependent, and increase as exposure to brexpiprazole increases.

It is not presently recognized in the art that the dosing regimen for brexpiprazole should be adjusted based on the body weight or obesity status of the patient, despite the fact that obesity and schizophrenia or depression are often comorbid conditions. While the REXULTI® label, for example, teaches that weight gain can be a side effect of treatment with brexpiprazole, or that being overweight is a risk factor for other side effects such as hyperglycemia, the label does not instruct any changes in dosing for obese or overweight patients compared to normal weight patients. Brexpiprazole dosing adjustments are only recommended based on the indication treated, hepatic or renal impairment status, drug interactions with CYP2D6 inhibitors, or CYP3A4 inhibitors or inducers.

SUMMARY OF THE INVENTION

The inventors have discovered that the pharmacokinetics of brexpiprazole are substantively different in obese patients, requiring dosing changes when initiating treatment with brexpiprazole to achieve the same clinical response: effective treatment of schizophrenia and major depressive disorder. Prior to this invention, the standard of care left such obese patients untreated or undertreated, delaying resolution of their condition.

The invention addresses additional complexities and identifies modified dosing regimens that are critical to safely and effectively initiate treatment with brexpiprazole. In various embodiments the present invention is directed, inter alia, to specific dose adjustments that avoid under-treatment but do not exceed known exposure levels which would expose patients to serious side effects. In various embodiments the present invention is directed, inter alia, to specific dosing regimens needed for different indications and for different CYP2D6 metabolizer status.

Expected Drug Profile

The expected blood plasma brexpiprazole concentrations during the initiation of brexpiprazole treatment (days 1-28) for patients with schizophrenia and major depressive disorder (MDD) according to the brexpiprazole FDA label (revised in March 2020) are shown in FIG. 1A and FIG. 1B, respectively. Because there was no recognition in the art that the dosing regimen for initiating treatment with brexpiprazole should be adjusted based on the obesity status of the patient, obesity status was not expected to affect the blood plasma concentration of brexpiprazole. In other words, obese patients with schizophrenia or major depressive disorder were expected to have qualitatively similar blood plasma concentrations as normal weight patients.

The present inventors are not aware of anything in the art which would contradict the use of the same brexpiprazole dosing regimen for obese and normal-weight patients disclosed in the FDA-approved label for brexpiprazole. It is acknowledged in the art that body size and obesity can have an effect on the pharmacokinetics of some drugs; however, the clinical relevance of this effect is highly dependent on the particular characteristics of that drug. For example, Hanley et al., in reviewing the effects of obesity on drug pharmacokinetics, found that appropriate drug dosing should be individualized to the particular drug at issue, and that the distribution of a drug in obese patients cannot be entirely predicted based on the physiochemical attributes of the drug (e.g., lipophilicity, hydrophilicity) alone. (Hanley et al., Effect of Obesity on the Pharmacokinetics of Drugs in Humans, Clin. Pharmacokinet 2010, 49(2): 70-87.) The pharmacokinetic studies leading to the approval of brexpiprazole did not include patients with $BMI>35 \text{ kg/m}^2$, and previous studies have found that the effect of weight on the pharmacokinetics of brexpiprazole was less than 20% and was not a significant determinant in brexpiprazole pharmacokinetics. The inventors are not aware of any evidence in the prior art that suggests that there is any clinically important effect of obesity on brexpiprazole pharmacokinetics that would require any difference in the brexpiprazole dosing regimen between obese and normal-weight patients. Thus, at the time of the present application, the FDA-approved dosing instructions for obese and normal weight patients are the same. However, the present invention is based on the discovery that a patient's body size significantly affects the time it takes a patient to reach therapeutic levels of brexpiprazole. See FIG. 2A and FIG. 2B.

Without this new information, it was not appreciated in the art that, using the instructions for brexpiprazole dosing found in the existing FDA-approved labels for brexpiprazole (at the time of the present disclosure), obese patients do not reach therapeutic levels of brexpiprazole as quickly as normal weight patients upon initiating brexpiprazole treatment; or alternatively stated, it has been discovered that it takes significantly longer to reach therapeutic levels of brexpiprazole in obese patients compared to normal-weight patients using the FDA-approved label's instructions.

The REXULTI® label teaches reducing the dose of brexpiprazole to half of the usual dosage if the patient is a CYP2D6 poor metabolizer (CYP2D6 PMs or simply "PMs"). Similarly, the present inventors have also found that the time required to reach therapeutic levels of brexpiprazole for obese patients who are also PMs, using the FDA-approved brexpiprazole dosing regimen (i.e., half of the recommended dose), is longer than for normal-weight PMs.

Thus, prior to the present invention, for obese patient populations (as described herein), the patient's psychiatric disorders (e.g., schizophrenia and major depressive disorder) were unknowingly left undertreated because these patients did not reach therapeutic concentrations in a similar time as normal-weight patient. Such unintended undertreatment of psychiatric disorders is potentially quite serious, as complications of untreated psychiatric disorders include suicide attempts, anxiety, depression, alcohol or drug abuse, inability to work or attend school, financial problems, homelessness, social isolation, health and medical problems, being victimized, and aggressive behavior.

Thus, the development of the presently disclosed new dosage regimens allow obese patients to reach therapeutic levels of brexpiprazole as quickly as normal-weight patients without putting them at risk of akathisia.

The present disclosure provides an alternative dosing regimen for treating a patient with a psychiatric disorder, such as schizophrenia or major depressive disorder, with brexpiprazole, wherein the patient has one or more of the following characteristics: (i) a BMI of at least about 35; (ii) % IBW of at least about 150%; (iii) waist size greater than about 42 inches; (iv) % body fat greater than about 40%; (v) % android body fat greater than about 40%; (vi) % gynoid body fat greater than about 40%; (vii) total body fat greater than about 40 kg; or (viii) CYP2D6 poor metabolizer.

The present inventors have discovered that patients dosed according to the brexpiprazole FDA label dosage instructions that have any of the aforementioned characteristics do not reach therapeutic levels of brexpiprazole as quickly as non-obese CYP2D6 EM patients. In particular, patients that are obese (e.g., have one or more of the following characteristics: (i) a BMI of at least about 35 kg/m$^2$; (ii) % IBW of at least about 150%; (iii) waist size greater than about 42 inches; (iv) % body fat greater than about 40%; (v) % android body fat greater than about 40%; (vi) % gynoid body fat greater than about 40%; (vii) total body fat greater than about 40 kg) or obese (as defined herein) CYP2D6 poor metabolizers (PM) take longer to reach the similar therapeutic concentrations of patients that are normal-weight CYP2D6 extensive metabolizers (EM) (FIG. 2A and FIG. 2B). The brexpiprazole dosage regimen recommended by the FDA label is shown in Table 1.

TABLE 1

Brexpiprazole Dosing According to FDA Label

| Indication | Starting Dose | Recommended Dose | Maximum Dose |
|---|---|---|---|
| Major depressive disorder (MDD) | 0.5-1 mg/day | 2 mg/day | 3 mg/day |
| Schizophrenia | 1 mg/day | 2-4 mg/day | 4 mg/day |

For adjunctive treatment for MDD, the FDA label recommends a starting dose of brexpiprazole of 0.5 mg, then titrating the starting dose of brexpiprazole up to 1 mg (if starting at 0.5 mg) once daily, and then up to the recommended dosage of 2 mg once daily. Alternatively, the FDA label recommends using a starting dose of 1 mg once daily, then titrating up to the recommended dosage of 2 mg once daily. Dosage increases should occur at weekly intervals based on the patient's clinical response and tolerability. The maximum daily dosage is 3 mg.

For treatment of schizophrenia, the label teaches starting with an initial or starting dose of 1 mg of brexpiprazole administered once daily on each of the first 4 days of treatment (days 1-4), then administering 2 mg once daily on the next 3 days of treatment (day 5 through day 7), and then administering 4 mg once daily on day 8 based on the patient's clinical response and tolerability. The maximum daily dosage is 4 mg.

The dosage for CYP2D6 poor metabolizers (patients classified as having a CYP2D6 enzyme phenotype with little or no CYP2D6 activity compared to normal levels of CYP2D6 activity) is half of the dose that would otherwise be administered if the patent was not a CYP2D6 poor metabolizer.

Applicants have developed a modified brexpiprazole dosage regimen for initiating treatment with brexpiprazole that allows obese patients and/or obese CYP2D6 PM (poor metabolizer) patients to reach therapeutically effective concentrations at a similar time compared to normal-weight CYP2D6 EM patients (extensive metabolizers; i.e., patients classified as having a CYP2D6 enzyme phenotype with normal levels of CYP2D6 activity) (FIGS. 3-9). As Table D of Example 2 reveals, one embodiment of the modified dosage regimen of the present invention provides double the total daily dose of brexpiprazole of the FDA label on days 1-7. As Table J in Example 3 reveals, other embodiments of the modified dosage regimen provide double the total daily dose of brexpiprazole of the FDA label on days 1-14 or days 1-21.

The FDA label for brexpiprazole (REXULTI® revised March 2020) neither recognizes that obese CYP2D6 EM patients and/or obese CYP2D6 PM patients do not reach therapeutic levels as quickly as normal-weight CYP2D6 EM patients, nor does it provide a dosage regimen that corrects this (hitherto unknown) problem. Instead, the label implicitly teaches that obese CYP2D6 EM should receive the same dose as normal-weight CYP2D6 EM, and explicitly teaches that all CYP2D6 PM patients (i.e., normal-weight and obese) should receive half of the dose that CYP2D6 EM patients receive. However, Applicants have discovered that administering the same dose to obese CYP2D6 EM that normal-weight CYP2D6 EM receive, and half of the dose to obese CYP2D6 PM (as taught by the FDA label) causes obese CYP2D6 EM and obese CYP2D6 PM patients to reach therapeutic brexpiprazole concentrations more slowly than normal-weight CYP2D6 EM patients. Administering brexpiprazole according to a modified dosage regimen provided herein enables obese and/or obese CYP2D6 PM patients to approach therapeutic levels of brexpiprazole as quickly as normal-weight CYP2D6 EM patients (FIGS. 3-9).

In embodiments, the disclosure provides method of initiating treatment of schizophrenia with brexpiprazole in an obese patient who is not a CYP2D6 poor metabolizer, comprising: (a) administering 1 mg brexpiprazole twice daily on each of the first 4 days of brexpiprazole treatment; (b) administering 2 mg brexpiprazole twice daily on each of the next 3 days following step (a); and then (c) administering a recommended dose of brexpiprazole once daily thereafter; wherein the obese patient has one or more of the following characteristics: (i) BMI of at least about 35; (ii) % IBW of at least about 150%; (iii) waist size greater than about 42 inches; (iv) % body fat greater than about 40%; (v) % android body fat greater than about 40%; (vi) % gynoid body fat greater than about 40%; or (vii) total body fat greater than about 40 kg. In embodiments, the recommended dose of brexpiprazole is 2-4 mg/day. In embodiments, the recommended dose of brexpiprazole is 2 mg/day. In embodiments, the recommended dose of brexpiprazole is 2.25 mg/day. In embodiments, the recommended dose of brexpiprazole is 2.5 mg/day. In embodiments, the recommended dose of brexpiprazole is 2.75 mg/day. In embodiments, the recommended dose of brexpiprazole is 3 mg/day. In embodiments, the recommended dose of brexpiprazole is 3.25 mg/day. In some embodiments, the recommended dose of brexpiprazole is 3.5 mg/day. In embodiments, the recommended dose of brexpiprazole is 3.75 mg/day. In embodiments, the recommended dose of brexpiprazole is 4 mg/day.

In embodiments, the disclosure provides a method of initiating treatment of schizophrenia with brexpiprazole in an obese patient who is a CYP2D6 poor metabolizer, comprising: (a) administering 0.5 mg brexpiprazole twice daily on each of the first 4 days of brexpiprazole treatment; (b) administering 1 mg brexpiprazole twice daily on each of the next 3 days following step (a); and then (c) administering half of a recommended daily dose of brexpiprazole once daily thereafter; wherein the obese patient has one or more of the following characteristics: (i) BMI of at least about 35; (ii) % IBW of at least about 150%; (iii) waist size greater than about 42 inches; (iv) % body fat greater than about 40%; (v) % android body fat greater than about 40%; (vi) % gynoid body fat greater than about 40%; or (vii) total body fat greater than about 40 kg. In embodiments, half of the recommended dose of brexpiprazole is 1-2 mg/day. In embodiments, half of the recommended dose of brexpiprazole is 1 mg/day. In embodiments, half of the recommended dose of brexpiprazole is 1.25 mg/day. In embodiments, half of the recommended dose of brexpiprazole is 1.5 mg/day. In embodiments, half of the recommended dose of brexpiprazole is 1.75 mg/day. In embodiments, half of the recommended dose of brexpiprazole is 2 mg/day.

In embodiments, the disclosure provides a method of initiating adjunctive treatment of major depressive disorder with brexpiprazole in an obese patient who is not a CYP2D6 poor metabolizer, comprising: (a) administering either 0.5 or 1 mg brexpiprazole twice daily on each of the first 7 days of brexpiprazole treatment; (b) administering double the individual brexpiprazole dose of step (a) once daily on each of the next 7 days following step (a); and then (c) administering the recommended daily dose of brexpiprazole once daily thereafter; wherein the obese patient has one or more of the following characteristics: (i) BMI of at least about 35; (ii) % IBW of at least about 150%; (iii) waist size greater than about 42 inches; (iv) % body fat greater than about 40%; (v) % android body fat greater than about 40%; (vi) % gynoid body fat greater than about 40%; or (vii) total body fat greater than about 40 kg. In embodiments of the method of initiating adjunctive treatment of major depressive disorder with brexpiprazole, step (a) is administering 0.5 mg brexpiprazole twice daily for each of the first 7 days of brexpiprazole treatment, and step (b) is administering 1 mg brexpiprazole once daily for each of the next 7 days following step (a). In embodiments of the method of initiating treatment of major depressive disorder with brexpiprazole, step (a) is administering 1 mg brexpiprazole twice daily for each of the first 7 days of brexpiprazole treatment, and step (b) is administering 2 mg brexpiprazole once daily for each of the next 7 days following step (a). In embodiments, the recommended daily dose of step (c) is 2-3 mg/day. In embodiments, the recommended daily dose of step (c) is 2 mg/day. In embodiments, the recommended daily dose of step (c) is 2.25 mg/day. In embodiments, the recommended daily dose of step (c) is 2.5 mg/day. In embodiments, the recommended daily dose of step (c) is 2.75 mg/day. In embodiments, the recommended daily dose of step (c) is 3 mg/day.

In embodiments, the disclosure provides a method of initiating adjunctive treatment of major depressive disorder with brexpiprazole in an obese patient who is a CYP2D6 poor metabolizer, comprising: (a) administering 0.5 mg brexpiprazole twice daily on each of the first 7 days of brexpiprazole treatment; (b) administering 1 mg twice daily on each of the next 7 days following step (a); and then (c) administering half of the recommended daily dose of brexpiprazole once daily thereafter; wherein the obese patient has one or more of the following characteristics: (i) BMI of at least about 35; (ii) % IBW of at least about 150%; (iii) waist size greater than about 42 inches; (iv) % body fat greater than about 40%; (v) % android body fat greater than about 40%; (vi) % gynoid body fat greater than about 40%; or (vii) total body fat greater than about 40 kg. In embodiments, half of the recommended daily dose of step (c) is 1-1.5 mg/day. In embodiments, half of the recommended daily dose of step (c) is 1 mg/day. In embodiments, half of the recommended daily dose of step (c) is 1.25 mg/day. In embodiments, half of the recommended daily dose of step (c) is 1.5 mg/day. In embodiments, half of the recommended daily dose of step (c) is 1.75 mg/day. In embodiments, half of the recommended daily dose of step (c) is 2 mg/day.

In embodiments, the disclosure provides method of initiating adjunctive treatment of major depressive disorder with brexpiprazole in an obese patient who is a CYP2D6 poor metabolizer, comprising: (a) administering 0.25 mg brexpiprazole twice daily on each of the first 7 days of brexpiprazole treatment; (b) administering 0.5 twice daily on each of next 7 days following step (a); (c) administering 1 mg daily twice on each of the next 7 days following step (b); and then (d) administering half of the recommended daily dose of brexpiprazole once daily thereafter; wherein the obese patient has one or more of the following characteristics: (i) BMI of at least about 35; (ii) % IBW of at least about 150%; (iii) waist size greater than about 42 inches; (iv) % body fat greater than about 40%; (v) % android body fat greater than about 40%; (vi) % gynoid body fat greater than about 40%; or (vii) total body fat greater than about 40 kg. In some embodiments, half of the recommended daily dose of step (c) is 1-1.5 mg/day. In some embodiments, half of the recommended daily dose of step (c) is 1 mg/day. In some embodiments, half of the recommended daily dose of step (c) is 1.25 mg/day. In some embodiments, half of the recommended daily dose of step (c) is 1.5 mg/day. In some embodiments, half of the recommended daily dose of step (c) is 1.75 mg/day. In some embodiments, half of the recommended daily dose of step (c) is 2 mg/day.

Applicant also surprisingly discovered that normal-weight CYP2D6 PM patients do not reach therapeutic levels as quickly as normal-weight CYP2D6 EM (FIG. 1A and FIG. 1B). Administering brexpiprazole according to a modified dosage regimen provided herein enables normal-weight CYP2D6 PM patients to approach therapeutic levels of brexpiprazole as quickly as normal-weight CYP2D6 EM patients (FIGS. 5, 11, and 12)

In embodiments, the disclosure provides a method of initiating treatment of schizophrenia with brexpiprazole in a normal-weight patient who is a CYP2D6 poor metabolizer, comprising: (a) administering 0.5 mg brexpiprazole twice daily on each of the first 4 days of brexpiprazole treatment; (b) administering 1 mg brexpiprazole twice daily on each of the next 3 days following step (a); and then (c) administering half of the recommended dose of brexpiprazole once daily thereafter, wherein the normal-weight patient has at least one of the following characteristics: (i) BMI less than about 35 kg/m$^2$; (ii) % IBW less than about 150%; (iii) waist size less than about 42 inches; (iv) % body fat less than about 40%; (v) % android body fat less than about 40%; (vi) % gynoid body fat less than about 40%; or (vii) total body fat less than about 40 kg. In embodiments, half of the recommended dose of brexpiprazole is 1-2 mg/day. In embodiments, half of the recommended dose of brexpiprazole is 1 mg/day. In embodiments, half of the recommended dose of brexpiprazole is 1.25 mg/day. In embodiments, half of the recommended dose of brexpiprazole is 1.5 mg/day.

In embodiments, the disclosure provides a method of initiating adjunctive treatment of major depressive disorder with brexpiprazole in a normal-weight patient who is not a CYP2D6 poor metabolizer, comprising: (a) administering either 0.25 or 0.5 mg brexpiprazole twice daily on each of the first 7 days of brexpiprazole treatment; (b) administering double the individual brexpiprazole dose of step (a) once daily on each of the next 7 days following step (a); and then (c) administering the recommended daily dose of brexpiprazole once daily thereafter; wherein the normal-weight patient has at least one of the following characteristics: (i) BMI less than about 35 kg/m$^2$; (ii) % IBW less than about 150%; (iii) waist size less than about 42 inches; (iv) % body fat less than about 40%; (v) % android body fat less than about 40%; (vi) % gynoid body fat less than about 40%; or (vii) total body fat less than about 40 kg. In embodiments of the method of initiating adjunctive treatment of major depressive disorder with brexpiprazole, step (a) is administering 0.25 mg brexpiprazole twice daily for each of the first 7 days of brexpiprazole treatment, and step (b) is administering 0.5 mg brexpiprazole once daily for each of the next 7 days following step (a). In embodiments of the method of initiating treatment of major depressive disorder with brexpiprazole, step (a) is administering 0.5 mg brexpiprazole twice daily for each of the first 7 days of brexpiprazole treatment, and step (b) is administering 1 mg brexpiprazole once daily for each of the next 7 days following step (a). In embodiments, half of the recommended dose of brexpiprazole is 1-1.5 mg/day. In embodiments, half of the recommended dose of brexpiprazole is 1 mg/day. In embodiments, half of the recommended dose of brexpiprazole is 1.25 mg/day. In embodiments, half of the recommended dose of brexpiprazole is 1.5 mg/day.

BRIEF DESCRIPTION OF THE FIGURES

FIG. 1B shows the plasma levels of brexpiprazole in normal-weight CYP2D6 EM and CYP2D6 PM patients with major depressive disorder (MDD) that are treated according to the brexpiprazole FDA label, with a starting dose of 0.5 mg. While steady-state brexpiprazole plasma levels in CYP2D6 PM patients are lower than brexpiprazole plasma levels in CYP2D6 EM patients, these steady-state levels are considered therapeutically effective concentrations for CYP2D6 PM patients.

FIG. 3 shows the plasma levels of brexpiprazole over time of obese CYP2D6 EM schizophrenia patients that are administered 1 mg brexpiprazole twice daily for days 1-4 and 2 mg BID for days 5-7 (Table 3. Modified Dosing Regimen 1). Obese CYP2D6 EM patients treated according to the disclosed modified dosage regimen reach therapeutic concentrations that are similar to normal-weight CYP2D6 EM patients treated according to the brexpiprazole FDA label.

FIG. 4 shows the plasma levels of brexpiprazole over time of obese CYP2D6 PM schizophrenia patients that are administered 0.5 mg brexpiprazole twice daily on days 1-4, 1 mg BID on days 5-7, and then are administered 2 mg brexpiprazole twice daily for days 8-14 (Table 3. Modified Dosing Regimen 2). Obese CYP2D6 PM patients treated according to the modified dosage regimen reach therapeutic concentrations of brexpiprazole in a similar time as normal-weight CYP2D6 EM patients treated according to the brexpiprazole FDA label. When administered brexpiprazole according to the FDA label, obese CYP2D6 PM patients do not reach therapeutic concentrations in the first 28 days of administration.

FIG. 5 shows the plasma brexpiprazole concentration over time of normal-weight CYP2D6 PM schizophrenia patients that are administered brexpiprazole according to the modified dosage regimen of Table D.

FIG. 6 shows the plasma levels of brexpiprazole over time of obese CYP2D6 EM major depressive disorder patients that are administered 0.5 mg brexpiprazole twice daily for the first seven days (Table 4. Modified Dosing Regimen A). Obese CYP2D6 EM patients treated according to the disclosed modified dosage regimen reach therapeutic concentrations that are similar to normal-weight CYP2D6 EM patients treated according to the brexpiprazole FDA label.

FIG. 7 shows the plasma levels of brexpiprazole over time of obese CYP2D6 EM major depressive disorder patients that are administered 1 mg brexpiprazole twice daily for the first seven days (Table 4. Modified Dosing Regimen B). Obese CYP2D6 EM patients treated according to the modified dosage regimen reach therapeutic concentrations of brexpiprazole in a similar time as normal-weight CYP2D6 EM patients treated according to the brexpiprazole FDA label.

DETAILED DESCRIPTION

Definitions

Any reference to brexpiprazole herein also encompasses all of the pharmaceutically acceptable isomers (e.g., stereoisomers), solvates, hydrates, polymorphs, salts, and prodrugs (e.g., esters and phosphates).

As used herein, "normal," "normal-weight," or other derivations or variations thereof refers to a non-obese state in a person who can have at least one of the following characteristics: BMI less than about 35 kg/m$^2$, % IBW less than about 150%, waist size less than about 42, % body fat less than about 40%, % android body fat less than about 40%, % gynoid body fat less than about 40%, and total body fat less than about 40 kg. Unless otherwise modified, "normal metabolizer" also means an extensive CYP2D6 metabolizer.

As used herein, the terms "reference dose", "reference daily dose", "recommended dose", or "usual dose" refer to the maintenance dosage of brexpiprazole, as indicated on the manufacture's FDA-approved label (e.g., the most recent FDA-approved label in effect as of March, 2020). The REXULTI® label also refers to a "Starting Dose" and a "Maximum Dose" as distinct from the "Recommended Dose". While colloquially the term "recommended" or "usual" dose could refer to any dose taught in the REXULTI® label, in this disclosure the term "recommended dose" refers more narrowly to doses recommended for maintenance treatment (including the "maximum dose" suitable for such treatment) of a normal weight, extensive CYP2D6 metabolizer patients. Thus, where the REXULTI® label teaches administering 2 mg once daily up to a maximum dose of 3 mg once daily for an MDD patient, such dose or dose range is a "recommended" dose or dose range. Where the REXULTI® label teaches reducing the "usual dosage by half" for "Known CYP2D6 Metabolizers", the recommended or usual dose as used herein is the dose "recommended" or "usual" for patients who are not CYP2D6 PMs.

It is common for a particular drug to be approved for multiple different indications, and each indication may have a different reference or recommended dose. For example, the "recommended dose" listed in the March 2020 REXULTI® label indicates that 2 to 3 mg once daily is the "recommended dose" for MDD and 2 to 4 mg once daily is the "recommended dose" for schizophrenia.

Figure 1A:
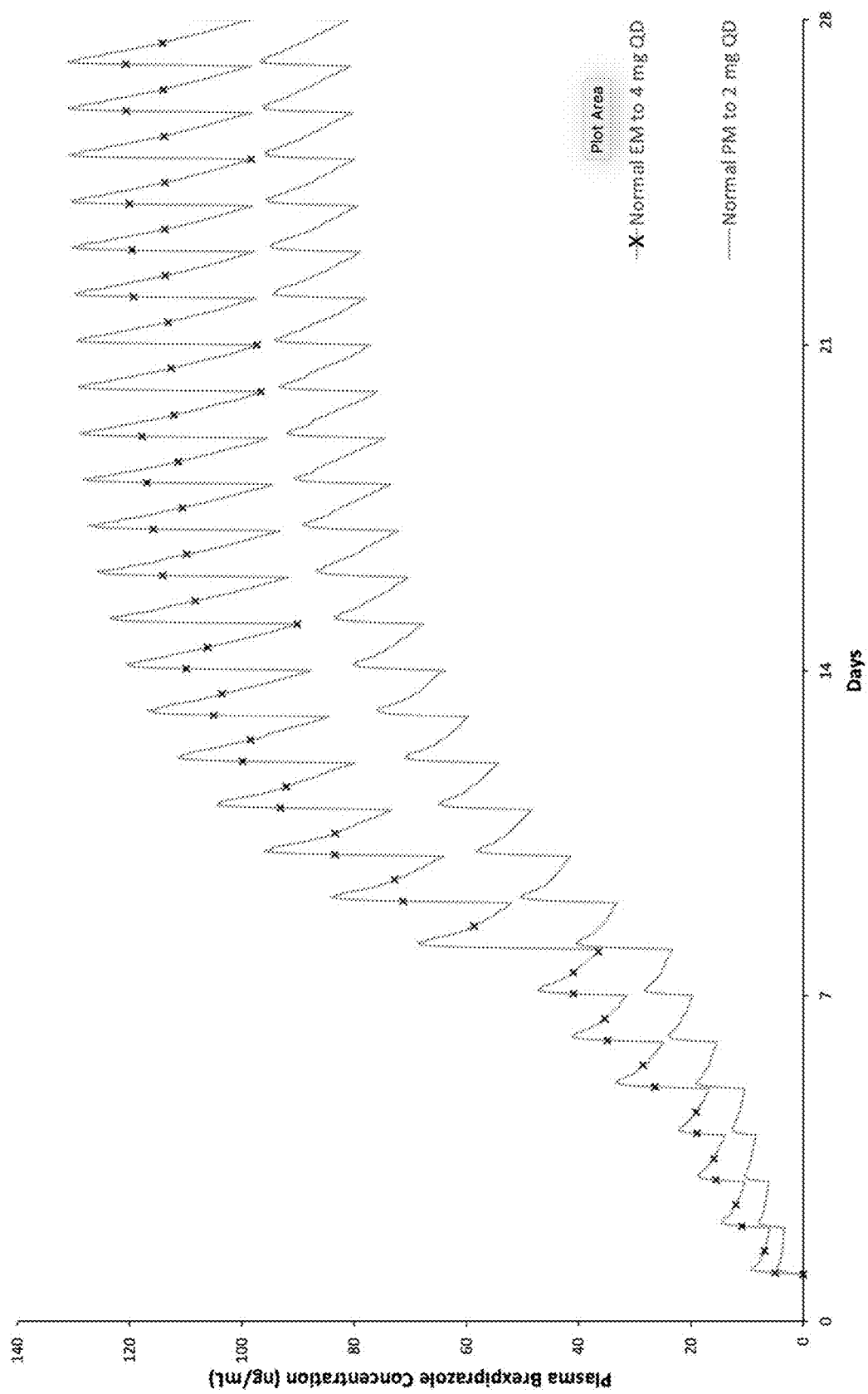
FIG. 1A shows the plasma levels of brexpiprazole in normal-weight CYP2D6 EM and CYP2D6 PM patients with schizophrenia that are treated according to the brexpiprazole FDA label. While steady-state brexpiprazole plasma levels of CYP2D6 PM patients are lower than brexpiprazole plasma levels of CYP2D6 EM patients, these steady-state levels are considered therapeutically effective concentrations for CYP2D6 PM patients.

As used herein "therapeutic concentration" refers to the steady state pharmacokinetic profile of brexpiprazole based on the pharmacokinetic studies supporting FDA approval of brexpiprazole as measured in normal-weight patients. As shown in FIG. 1A and FIG. 1B, normal-weight patients treated with brexpiprazole achieve steady state pharmacokinetics after the initiation phase of treatment, typically around days 14-21 of treatment according to FIG. 1A and FIG. 1B. Because the blood plasma levels in FIG. 1A and FIG. 1B represent averages from all patients, some deviation from the average steady state pharmacokinetic profile in a particular patient or patient population is expected and is acceptable in the art. The modified dosing regimens of the present disclosure bring the blood plasma concentrations of brexpiprazole in obese patients and obese CYP2D6 PM patients within appropriate degrees of variation of the average steady state pharmacokinetic profile of normal-weight CYP2D6 EM patients shown in FIG. 1A and FIG. 1B. This enables obese patients or obese CYP2D6 PM patients to reach therapeutic concentrations of brexpiprazole at a similar time as normal-weight CYP2D6 EM patients, allowing for better clinical response. It is not necessary for the pharmacokinetic profile of the modified dosing regimens disclosed herein to overlap exactly with the pharmacokinetic profile of brexpiprazole based on the pharmacokinetic studies supporting FDA approval.

As used herein "BID" refers to twice daily administration.

As used herein "QD" refers to once daily administration.

Brexpiprazole

Brexpiprazole is an atypical antipsychotic, available as REXULTI®, to be used as an adjunctive therapy to antidepressants for the treatment of major depressive disorder and as a treatment for schizophrenia. The FDA label of REXULTI® (Otsuka and Lundbeck, revised March 2020) is incorporated by reference herein in its entirety. Brexiprazole is 7-{4-[4-(1-Benzothiophen-4-yl)piperazin-1-yl]butoxy}quinolin-2(1H)-one. The empirical formula is $C_{25}H_{27}N_3O_2S$ and its molecular weight is 433.57.

The chemical structure of brexpiprazole is

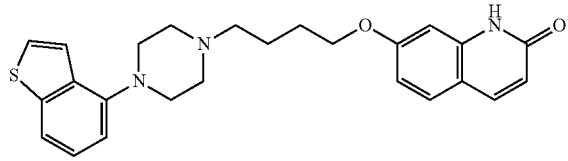 [SMILES: O=c1ccc2ccc(OCCCCN3CCN(c4cccc5sccc45)CC3)cc2[nH]1]

The FDA label provides the following dosage instructions for adjunctive treatment for major depressive disorder: The starting dosage for brexpiprazole (REXULTI®) as adjunctive treatment is 0.5 mg or 1 mg once daily, taken orally with or without food. Titrate to 1 mg once daily, then up to the recommended dosage of 2 mg once daily. Dosage increases should occur at weekly intervals based on the patient's clinical response and tolerability. The maximum recommended daily dosage is 3 mg. Periodically reassess to determine the continued need and appropriate dosage for treatment.

The FDA label provides the following dosage instructions for schizophrenia: The starting dosage for brexpiprazole (REXULTI®) is 1 mg once daily on Days 1 to 4, taken orally with or without food. The recommended brexpiprazole (REXULTI®) dosage is 2 mg to 4 mg once daily. Titrate to 2 mg once daily on Day 5 through Day 7, then to 4 mg on Day 8 based on the patient's clinical response and tolerability. The maximum daily dosage is 4 mg.

The FDA label provides dosage modifications for CYP2D6 Poor Metabolizers and for concomitant use with CYP Inhibitors or Inducers: Dosage adjustments are recommended in patients who are known cytochrome P450 (CYP) 2D6 poor metabolizers and in patients taking concomitant CYP3A4 inhibitors or CYP2D6 inhibitors or strong CYP3A4 inducers (see Table 2). If the coadministered drug is discontinued, adjust the REXULTI dosage to its original level. If the coadministered CYP3A4 inducer is discontinued, reduce the REXULTI dosage to the original level over 1 to 2 weeks.

TABLE 2

| Factors | Adjusted Brexpiprazole (REXULTI ®) Dosage |
|---|---|
| CYP2D6 Poor Metabolizers | |
| CYP2D6 poor metabolizers | Administer half of the usual dose. |
| Known CYP2D6 poor metabolizers taking strong/moderate CYP3A4 inhibitors | Administer a quarter of the usual dose. |
| Patients taking CYP2D6 Inhibitors and/or CYP3A4 Inhibitors | |
| Strong CYP2D6 inhibitors (paroxetine, fluoxetine) | Administer half of the usual dose. |
| Strong CYP3A4 inhibitors | Administer half of the usual dose. |
| Strong/moderate CYP2D6 inhibitors with strong/moderate CYP3A4 inhibitors | Administer a quarter of the usual dose. |
| Patients taking CYP3A4 Inducers | |
| Strong CYP3A4 Inducers | Double usual dose over 1 to 2 weeks |

Applicant found that the brexpiprazole (REXULTI®) dosage instructions for initiating treatment with brexpiprazole do not provide therapeutically effective levels of brexpiprazole for patients that are obese or obese CYP2D6 PM as quickly as for normal-weight CYP2D6 EMs.

Dosage Regimens

Figure 10:
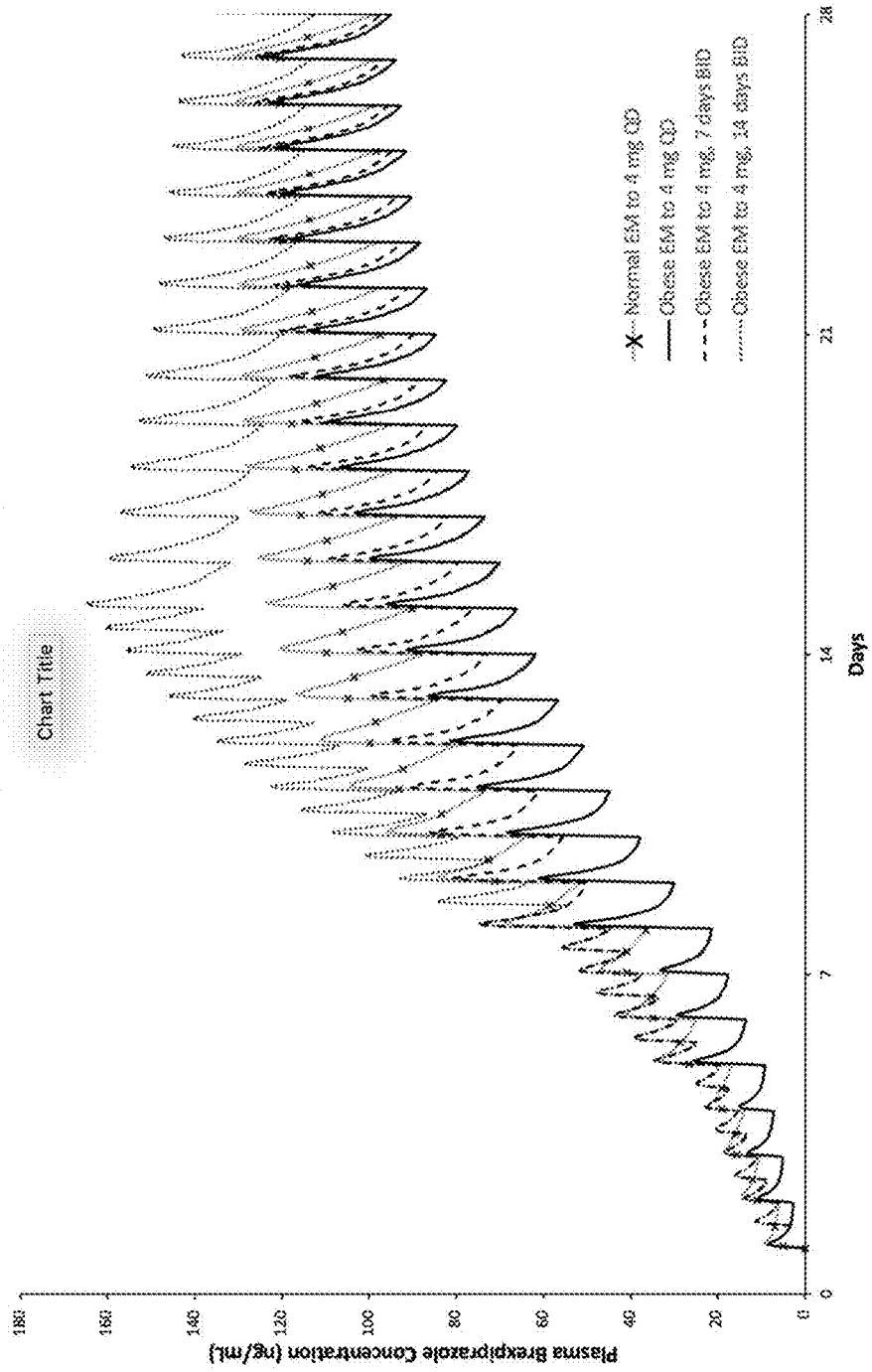
FIG. 10 shows the plasma levels of brexpiprazole over time for an obese CYP2D6 EM when the patient is administered brexpiprazole (i) according to the brexpiprazole FDA label; (ii) BID for 7 days according to a modified dosing regimen of the disclosure; and (iii) BID for 14 days. When BID dosing exceeds the modified dosing of the disclosure, plasma levels elevate significantly above those of normal-weight CYP2D6 EM and present a risk of serious side effects.
Figure 13:
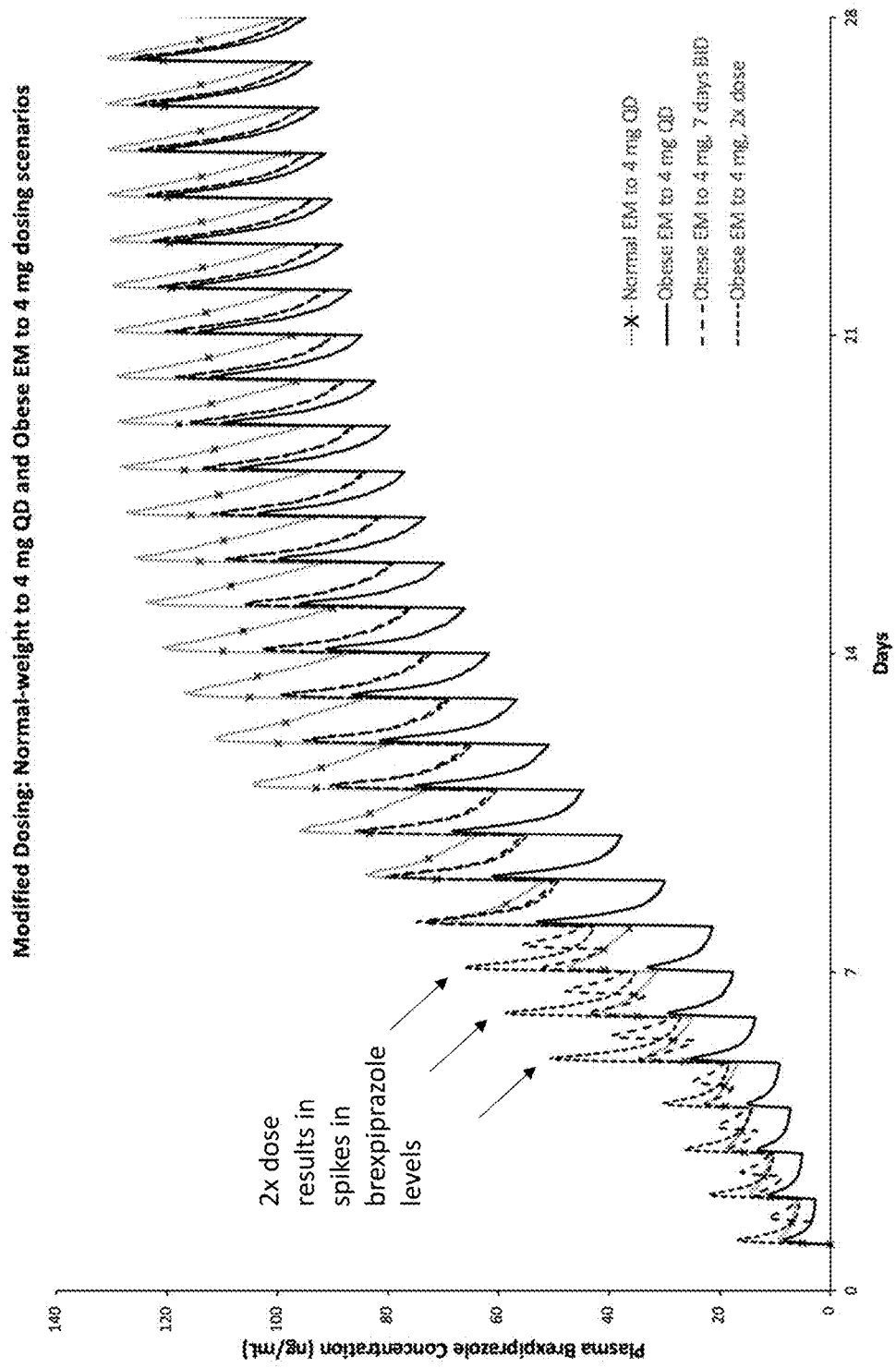
FIG. 13 shows the plasma levels of brexpiprazole over time of obese CYP2D6 EM major depressive disorder patients that are administered double the daily dose once daily ("Obese EM to 4 mg, 2× dose").

The various dosing methods of the present invention, as described herein, comprise initiating treatment by administering an elevated daily dose of brexpiprazole for one or more defined time periods, then at an appropriate time (as described herein), administering the FDA-recommended dose appropriate for the indication (e.g., schizophrenia or major depressive disorder). The initial, elevated daily dose is administered in the form of multiple daily doses, as a single elevated dose would result in sharp "peaks" in the plasma level that could cause serious side effects such as akathisia. FIG. 13. The multiple daily brexpiprazole doses administered at the initiation of brexpiprazole treatment according to various embodiments of the present invention are typically administered in the form of two equal daily doses, that when combined provided a daily dose of brexpiprazole that is higher than the starting dose of brexpiprazole described in the REXULTI® label. Typically, the multiple daily brexpiprazole doses administered at the initiation of brexpiprazole treatment provide a daily dose that is double the starting dose of brexpiprazole described in the REXULTI® label. However, in view of the discovery described herein, the initial dose of brexpiprazole according to the present invention could comprise unequal doses, and/or could be administered in more than two (e.g., three or four) daily doses. Alternatively, instead of administering multiple daily doses at the initiation of brexpiprazole treatment, the starting doses described herein (e.g. double the starting dose of brexpiprazole described in the REXULTI® label) may be administered once daily in a sustained or extended release formulation. Such a formulation can release brexpiprazole over the course of a day in a manner that is similar to twice (or more) daily administration of brexpiprazole. The guiding principle for initiating administration of brexpiprazole according to the methods disclosed herein is to increase the daily dose of brexpiprazole for a defined period such that obese CYP2D6 EM or obese CYP2D6 PM patients reach therapeutic plasma levels of brexpiprazole more quickly than would be obtained for such patients using the dosing regimens provided in FDA-approved brexpiprazole labels prior to the present invention. Further, the use of multiple daily doses (e.g., BID dosing) to provide such elevated daily doses of brexpiprazole (e.g., elevated relative to the daily "Starting Dose" and/or "Recommended Dose" provided in REXULTI® labels published prior to the present invention) are designed to ensure that no single dose elevates the brexpiprazole plasma levels of such patients to levels which would increase the risk of serious side effects such as akathisia. The limited duration of such multiple dosing prior to reverting to the recommended or usual maintenance dose of brexpiprazole is also designed to prevent elevated plasma levels of brexpiprazole that could increase the risk of serious side effects such as akathisia. FIG. 10 shows the effect of BID dosing in an obese schizophrenia patient during the first 14 days of treatment. After 7 days of BID dosing, the plasma levels of brexpiprazole begin to elevate above the blood plasma levels that would occur in normal-weight patients treated according to the FDA label, and the increased exposure becomes more pronounced and potentially more dangerous each day of BID treatment through day 14. This results in blood plasma concentrations that present an unacceptable risk of serious side effects.

The skilled artisan understands that in various embodiments, the magnitude and/or number of initial doses of brexpiprazole can be varied, along with the duration of the initial dosing period, such that the obese patients (EM and PM) according to the present invention reach therapeutic plasma levels of brexpiprazole more rapidly than they would if using the dosing regimens provided in FDA-approved brexpiprazole labels prior to the present invention, without increasing the risk of serious side effects.

The skilled artisan understands that the REXULTI® label (March 2020) contains provisions for dose adjustments in the case of concomitant use with a strong CYP2D6 or strong CYP3A4 inhibitor (e.g., administer half of the dose), or concomitant use with a strong CYP2D6 and strong CYP3A4 inhibitor (e.g., administer a quarter of the dose). These dose adjustments are applied to any relevant recommended dose or patient population.

In some embodiments, the modified dosage regimens described herein provide therapeutically effective levels of brexpiprazole for certain patient populations (e.g., for patients that are obese or are obese CYP2D6 poor metabolizers).

In some embodiments, the modified dosage regimens of the present invention provide a starting dose. As used herein, a "starting dose" is the lowest dose of brexpiprazole that is administered when initiating treatment with brexpiprazole. In some embodiments, the starting dose is administered on day 1 of brexpiprazole treatment. In some embodiments, the starting dose is administered on days 1-4 of brexpiprazole treatment. In some embodiments, the starting dose is administered on days 1-7 of brexpiprazole treatment. In some embodiments, the starting dose of the modified brexpiprazole dosage regimens of the present invention is double that of the starting dose instructed by the brexpiprazole (REXULTI®) FDA label (March 2020). In some embodiments, the starting dose of the modified brexpiprazole dosage regimen is triple that instructed by the brexpiprazole (REXULTI®) FDA label (March 2020). In some embodiments, the starting dose on days 1-4 of the modified brexpiprazole dosage regimen is double that of the starting dose instructed by the brexpiprazole (REXULTI®) FDA label (March 2020) for days 1-4. In some embodiments, the starting dose on days 1-7 of the modified brexpiprazole dosage regimen is double that of the starting dose instructed by the brexpiprazole (REXULTI®) FDA label (March 2020) for days 1-7. In some embodiments, the dose administered on days 8-14 or days 8-21 of the modified brexpiprazole dosage regimen is double that of the dose instructed by the brexpiprazole (REXULTI®) FDA label (March 2020) for days 8-14 or days 8-21. As used herein, phrases such as "days 1-4", "days 5-7", "days 1-7" and the like refer to days after first initiating the administration of brexpiprazole. That is, "day 1" is the first day brexpiprazole is administered to the patient upon initiating treatment, day 7 is the seventh day of brexpiprazole treatment, etc. Initiating brexpiprazole treatment can refer to the first administration to a brexpiprazole-naive patient who has never been administered brexpiprazole, or to a patient who may have been administered brexpiprazole in the past, but has ceased treatment with brexpiprazole for a period sufficient to require re-introduction of brexpiprazole with a lower starting dose of brexpiprazole before increasing to the recommended dose.

In some embodiments, a patient is administered a starting dose of about 0.25 mg to about 3 mg of brexpiprazole, for example, about 0.25, about 0.5 mg, about 0.75 mg, about 1 mg, about 1.25 mg, about 1.5 mg, about 1.75 mg, about 2 mg, about 2.25 mg, about 2.5 mg, about 2.75 mg, or about 3 mg of brexpiprazole. In some embodiments, a patient is administered a total daily dose of 0.5 mg brexpiprazole on days 1-4 or days 1-7 (depending on the patient's condition). In some embodiments, a patient is administered a total daily dose of 1 mg brexpiprazole on days 1-4 or days 1-7 (depending on the patient's condition). In some embodiments, a patient is administered a total daily dose of 1.5 mg brexpiprazole on days 1-4 or days 1-7 (depending on the patient's condition). In some embodiments, a patient is administered a total daily dose of 2 mg brexpiprazole on days 1-4 or days 1-7 (depending on the patient's condition).

In various embodiments, any of the starting doses described herein are administered as two equal doses, twice per day (BID) for a defined period of time, e.g., for 1, 2, 3, 4, 5, 6, or 7 days, or any combination or range thereof. In some embodiments, a patient is administered 0.25 mg brexpiprazole twice daily on days 1-7. In some embodiments, a patient is administered 0.5 mg brexpiprazole twice daily brexpiprazole on days 1-4 or days 1-7 (depending on the patient's condition). In some embodiments, a patient is administered 0.75 mg brexpiprazole twice daily brexpiprazole on days 1-4 or days 1-7 (depending on the patient's condition). In some embodiments, a patient is administered 1 mg brexpiprazole twice daily on days 1-4 or days 1-7 (depending on the patient's condition).

In some embodiments, the dose of brexpiprazole is increased from the starting dose. In some embodiments, the dose of brexpiprazole is increased every 2-3 days, every 3-4 days, every 4-5 days, or every 6-7 days. In some embodiments, the dose of brexpiprazole is increased every week, every two weeks, every three weeks, or every month. In some embodiments, on day 5 of brexpiprazole administration, the dose of brexpiprazole is double that of the dose provided on the FDA label for day 5. In some embodiments, on day 8 of brexpiprazole administration, the dose of brexpiprazole is double that of the dose provided on the FDA label for day 8. In some embodiments, on day 15 of brexpiprazole administration, the dose of brexpiprazole is double that of the dose provided on the FDA label for day 15.

In some embodiments, the dose of brexpiprazole is increased from the starting dose by an amount ranging from about 0.25 mg to about 2 mg, for example, about 0.25 mg, about 0.5 mg, about 1 mg, about 1.5 mg, or about 2 mg, including all values and ranges in between. In some embodiments, the dose of brexpiprazole is increased by an amount ranging from about 0.25 mg to about 6 mg, for example, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, or about 6 mg, every 2-3 days, every 3-4 days, every 4-5 days, or every 6-7 days, including all values and ranges therebetween. In some embodiments, the dose of brexpiprazole is increased by an amount ranging from about 0.5 mg to about 6 mg, for example, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, or about 6 mg, every week, every two weeks, every three weeks, or every month, including all values and ranges therebetween. In some embodiments, on day 5 of brexpiprazole administration, the dose of brexpiprazole is doubled from the starting dose. In some embodiments, on day 8 of brexpiprazole administration, the dose of brexpiprazole is doubled from the starting dose.

Schizophrenia

In some embodiments, an obese CYP2D6 EM patient or obese CYP2D6 PM patient is administered a starting dose of 1 mg or 2 mg brexpiprazole as a total daily dose on days 1-4, according to the modified dosing regimens disclosed herein. In some embodiments, an obese CYP2D6 EM patient or obese CYP2D6 PM patient is administered a starting dose of 0.5 mg or 1 mg brexpiprazole, twice daily, on days 1-4, according to the modified dosing regimens disclosed herein.

In some embodiments, on day 5, the dose of brexpiprazole is increased from the starting dose. In some embodiments, the dose of brexpiprazole is increased on day 5 and maintained for the duration of brexpiprazole use. In some embodiments, the dose of brexpiprazole is increased on day 5, and the increased dose is administered from days 5-7. In some embodiments, the total daily dose administered on days 5-7 is 2-4 mg (2 mg, 2.5 mg, 3 mg, 3.5 mg, or 4 mg, inclusive of all values and ranges therebetween). In some embodiments, the dose administered on days 5-7 is 1-2 mg (e.g., 1 mg, 1.5 mg, or 2 mg, inclusive of all values and ranges therebetween) brexpiprazole twice daily.

In some embodiments, the patient resumes administration of the recommended daily dose starting on day 8. In some embodiments, an obese CYP2D6 EM patient or obese CYP2D6 PM patient is administered 2-4 mg (2 mg, 2.5 mg, 3 mg, 3.5 mg, or 4 mg, inclusive of all values and ranges therebetween) on day 8.

In some embodiments, on day 8, the dose of brexpiprazole is increased from the starting dose. In some embodiments, on day 8, the dose of brexpiprazole is increased from the dose administered on days 5-7. In some embodiments, the dose of brexpiprazole is increased on day 8, from the starting dose or from the dose administered on days 5-7. In some embodiments, the dose of brexpiprazole is increased on day 8 and maintained for the duration of brexpiprazole use. In some embodiments, the dose of brexpiprazole is increased on day 8, from the starting dose or from the dose administered on days 5-7, wherein the increase is maintained for days 8-14 of brexpiprazole use. In some embodiments, the dose administered on days 8-14 is 1-4 mg (1 mg, 1.5 mg, 2 mg, 2.5 mg, 3 mg, 3.5 mg, or 4 mg, inclusive of all values and ranges therebetween) as a total daily dose. In some embodiments, the dose administered on days 8-14 is 1-2 mg (e.g., 1 mg, 1.5 mg, or 2 mg, inclusive of all values and ranges therebetween) brexpiprazole twice daily.

In some embodiments, the patient resumes administration of the recommended daily dose starting on day 15. In some embodiments, an obese CYP2D6 EM patient or obese CYP2D6 PM patient is administered 2-4 mg (2 mg, 2.5 mg, 3 mg, 3.5 mg, or 4 mg, inclusive of all values and ranges therebetween) on day 15.

In some embodiments, a dose of about 0.5 mg to about 1 mg of brexpiprazole is administered twice daily on days 1-4, a dose of about 1 mg to about 2 mg of brexpiprazole is administered twice daily on days 5-7, and about 2 mg to about 4 mg of brexpiprazole is administered once daily or twice daily starting on day 8. In some embodiments, a dose of about 0.5 mg to about 1 mg of brexpiprazole is administered twice daily on days 1-4, a dose of about 1 mg to about 2 mg of brexpiprazole is administered twice daily on days 5-7, about 2 mg to about 4 mg of brexpiprazole is administered once daily or twice on days 8-15, and about 2-4 mg brexpiprazole is administered once daily starting on day 15. In some embodiments, a dose of about 0.5 mg brexpiprazole is administered twice daily on days 1-4, a dose of about 1 mg of brexpiprazole is administered twice daily on days 5-7, about 2 mg of brexpiprazole is administered twice daily on days 8-15, and about 1-2 mg brexpiprazole is administered once daily starting on day 15. In some embodiments, a dose of about 1 mg brexpiprazole is administered twice daily on days 1-4, a dose of about 2 mg of brexpiprazole is administered twice daily on days 5-7, about 2-4 mg of brexpiprazole is administered once daily starting on day 8-15. In some embodiments, a dose of about 0.5 mg brexpiprazole is administered twice daily on days 1-4, a dose of about 1 mg of brexpiprazole is administered twice daily on days 5-7, about 1-2 mg of brexpiprazole is administered once daily starting on day 8. In some embodiments, a dose of about 1 mg brexpiprazole is administered twice daily on days 1-4, a dose of about 2 mg of brexpiprazole is administered twice daily on days 5-7, about 2-4 mg of brexpiprazole is once daily starting on day 8.

In some embodiments, a total daily dose of about 1 mg to about 2 mg of brexpiprazole is administered on days 1-4, a total daily dose of about 2 mg to about 4 mg of brexpiprazole is administered on days 5-7, and a total daily dose of between about 2-4 mg of brexpiprazole is administered starting on day 8.

In some embodiments, the dose of brexpiprazole is increased from the starting dose on day 5 and maintained for days 5-7, and then decreased to the recommended daily dose on day 8 for the duration of brexpiprazole use. In some embodiments, the dose of brexpiprazole is increased from the starting dose on day 5 and maintained for days 5-7, then increased again on day 8 and maintained from days 8-14, and decreased to the recommended daily dose on day 15 for the duration of brexpiprazole use. In some embodiments, the dose administered on day 15 is 1 mg, 2 mg, 3 mg, or 4 mg.

In some embodiments, the patient with schizophrenia is an obese patient who is not a CYP2D6 poor metabolizer (in other words, the patient is an obese CYP2D6 EM patient), and the method comprises: (a) administering 1 mg brexpiprazole twice daily on each of the first 4 days of brexpiprazole treatment; (b) administering 2 mg brexpiprazole twice daily on each of the next 3 days following step (a); and then (c) administering a recommended dose of brexpiprazole (2-4 mg/day) once daily thereafter. In some embodiments, the patient with schizophrenia is an obese patient who is a CYP2D6 poor metabolizer, and the method comprises: (a) administering 0.5 mg brexpiprazole twice daily on each of the first 4 days of brexpiprazole treatment; (b) administering 1 mg brexpiprazole twice daily on each of the next 3 days following step (a); and then (c) administering half of a recommended daily dose of brexpiprazole (e.g., 1-2 mg/day) once daily thereafter.

In some embodiments, a patient with schizophrenia is treated with a modified dosage regimen as found in Table 3. The dosage found in Table 3 is the total daily dose of brexpiprazole. In some embodiments, the total daily dose is divided into two doses, for example, a patient that is administered a total daily dose of 4 mg brexpiprazole may be administered a first dose of 2 mg brexpiprazole and a second dose of 2 mg brexpiprazole.

TABLE 3

Dosing Regimens for Schizophrenia

| Dosage Regimen | Days 1-4 | Days 5-7 | Days 8-14 | Days 15+ | Weight | CYP2D6 Status |
|---|---|---|---|---|---|---|
| FDA Label | 1 mg (QD) | 2 mg (QD) | 2-4 mg (QD) | 2-4 mg (QD) | All | EM |
| FDA Label | 0.5 mg (QD) | 1mg (QD) | 1-2 mg (QD) | 1-2 mg (QD) | All | PM |
| Modified Dosing Regimen 1 | 2 mg (1 mg BID) | 4 mg (2 mg BID) | 2-4 mg (QD) | 2-4 mg (QD) | Obese | EM |
| Modified Dosing Regimen 2 | 1 mg (0.5 mg BID) | 2 mg (1 mg BID) | 2-4 mg (1-2 mg BID) | 1-2 mg (QD) | Obese | PM |
| Modified Dosing Regimen 3 | 1 mg (0.5 mg BID) | 2 mg (1 mg BID) | 1-2 mg (QD) | 1-2 mg (QD) | Non-obese | PM |

Adjunctive Treatment of Major Depressive Disorder

In some embodiments, an obese CYP2D6 EM patient or obese CYP2D6 PM patient is administered, as a starting daily dose, a total daily dose of 0.5 mg, 1 mg or 2 mg brexpiprazole on days 1-7, according to the modified dosing regimens disclosed herein. In some embodiments, an obese patient or obese CYP2D6 PM patient is administered a starting dose of 0.25 mg, 0.5 mg, or 1 mg brexpiprazole twice daily on days 1-7, according to the modified dosing regimens disclosed herein In some embodiments, on day 8, the dose of brexpiprazole is increased from the starting dose. In some embodiments, the dose of brexpiprazole is increased on day 8 and maintained for the duration of brexpiprazole use. In some embodiments, the dose of brexpiprazole is increased on day 8, and the increased dose is administered from days 8-14. In some embodiments, the patient resumes administration of the recommended daily dose starting on day 8 or starting on day 15. In some embodiments, the total daily dose of brexpiprazole administered on days 8-14 is 1-4 mg (e.g., 1 mg, 1.5 mg, 2 mg, 2.5 mg, 3 mg, 3.5 mg, or 4 mg, inclusive of all values and ranges therebetween). In some embodiments, 0.5-2 mg (0.5 mg, 1 mg, 1.5 mg, or 2 mg, inclusive of all values and ranges therebetween) is administered twice daily on days 8-14.

In some embodiments, the dose of brexpiprazole is increased on day 15, from the dose administered on days 8-14 of brexpiprazole use. In some embodiments, the dose of brexpiprazole is increased on day 15 from the dose administered on days 8-14 and maintained for the duration of brexpiprazole use. In some embodiments, the dose of brexpiprazole is increased on day 15 from the dose administered on days 8-14, and the dose is administered on days 15-21 of brexpiprazole treatment. In some embodiments, the total daily dose of brexpiprazole administered on days 15-21 is 1-6 mg (e.g., 1 mg, 1.5 mg, 2 mg, 2.5 mg, 3 mg, 3.5 mg, 4 mg, 4.5 mg, 5 mg, 5.5 mg, or 6 mg, inclusive of all values and ranges therebetween). In some embodiments, 0.5-3 mg (0.5 mg, 1 mg, 1.5 mg, 2 mg, 2.5 mg, or 3 mg, inclusive of all values and ranges therebetween) is administered twice daily on days 8-14.

In some embodiments, patients resume administration of the recommended daily dose starting on day 22.

In some embodiments, the dose of brexpiprazole is increased on day 8 from the starting dose. In some embodiments, the dose administered on day 8 is double the starting dose administered on day 1. In some embodiments, the starting dose of brexpiprazole is 0.25 mg, 0.5 mg, 1 mg, or 2 mg. In some embodiments, the dose of brexpiprazole administered on days 8-14 is 0.5 mg, 1 mg, or 2 mg.

In some embodiments, the dose of brexpiprazole is increased from the starting dose on day 8 and maintained for days 8-14, increased again on day 14 and maintained from days 14-21, and decreased to the recommended daily dose on day 22 for the duration of brexpiprazole use. In some embodiments, the dose of brexpiprazole administered on starting on day 22 is 1 mg, 1.5 mg, 2 mg, or 3 mg.

In some embodiments, the dose of brexpiprazole is increased from the starting dose on day 8 and maintained for days 8-14, and then decreased to the recommended daily dose on day 15 for the duration of brexpiprazole use. In some embodiments, the dose of brexpiprazole administered on starting on day 15 is 1 mg, 1.5 mg, 2 mg, or 3 mg.

In some embodiments, a patient is administered a starting dose of 2 mg on days 1-7, a total daily dose of 4 mg on days 8-14, a total daily dose of 2-3 mg starting on day 15 and for the duration of brexpiprazole use.

In some embodiments, a total daily dose of about 0.5 mg to about 2 mg of brexpiprazole is administered on days 1-7, a total daily dose of about 1 mg to about 4 mg of brexpiprazole is administered on days 8-14, and a total daily dose of between about 1-6 of brexpiprazole is administered starting on day 15. In some embodiments, a total daily dose of about 0.5 mg to about 1 mg of brexpiprazole is administered on days 1-7, a total daily dose of about 1 mg to about 2 mg of brexpiprazole is administered on days 8-14, and a total daily dose of about 2-3 mg of brexpiprazole is administered starting on day 15. In some embodiments, a total daily dose of about 0.5 mg of brexpiprazole is administered on days 1-7, a total daily dose of about 1 mg of brexpiprazole is administered on days 8-14, a total daily dose of about 2 mg is administered on days 14-21, and a total daily dose of 2-3 mg is administered starting on day 22 and for the duration of treatment. In some embodiments, a total daily dose of about 1 mg of brexpiprazole is administered on days 1-7, a total daily dose of about 1 mg of brexpiprazole is administered on days 8-14, a total daily dose of between about 2 mg is administered on days 14-21, and a total daily dose of 2-3 mg is administered starting on day 22 and for the duration of treatment. In some embodiments, a total daily dose of about 0.5 mg of brexpiprazole is administered on days 1-7, a total daily dose of about 1 mg of brexpiprazole is administered on days 8-14, a total daily dose of about 1-1.5 mg is administered on days 14-21, and a total daily dose of 1-1.5 mg is administered starting on day 22 and for the duration of treatment.

In some embodiments, a dose of about 0.25 mg to about 1 mg of brexpiprazole is administered twice daily on days 1-7, a dose of about 0.5 mg to about 4 mg of brexpiprazole is administered on days 8-14, and about 1 mg to about 3 mg of brexpiprazole is administered starting on day 15. In some embodiments, a dose of about 0.25 mg to about 1 mg of brexpiprazole is administered twice daily on days 1-7, a dose of about 0.5 mg to about 2 mg of brexpiprazole is administered twice daily on days 8-14, about 1 mg to about 3 mg of brexpiprazole is administered once daily starting on day 15. In some embodiments, a dose of about 0.25 mg to about 1 mg of brexpiprazole is administered twice daily on days 1-7, a dose of about 0.5 mg to about 1 mg of brexpiprazole is administered twice daily on days 8-14, a dose of about 1 mg to about 2 mg of brexpiprazole is administered twice daily on days 14-21, and dose of about 1 mg to about 1.5 mg is administered starting on day 22.

In some embodiments, about 0.5 or 1 mg brexpiprazole is administered twice daily on days 1-7 days, and then an increased dose of about 1 mg to about 2 mg of brexpiprazole is administered twice daily on days 8-14, and then from about 1 mg to about 3 mg brexpiprazole is administered once daily starting on day 15. In some embodiments, about 0.5 mg brexpiprazole is administered twice daily on days 1-7, about 1 mg of brexpiprazole is administered twice daily on days 8-14, and then about 2 mg to about 3 mg is administered once daily starting on day 15. In some embodiments, about 1 mg brexpiprazole is administered twice daily on days 1-7, about 2 mg of brexpiprazole is administered once daily on days 8-14, and then about 2 mg to about 3 mg is administered once daily starting on day 15.

In some embodiments, about 0.25 or 0.5 mg brexpiprazole is administered twice daily on days 1-7 of brexpiprazole treatment, an increased dose of 0.5 mg or about 1 mg brexpiprazole is administered twice daily on days 8-14, an increased dose of 1-1.5 mg brexpiprazole is administered twice daily on days 15-21, and a dose from about 1 mg to about 1.5 mg is administered starting on day 22. In some embodiments, about 0.25 mg brexpiprazole is administered twice daily on days 1-7 of brexpiprazole treatment, about 0.5 mg brexpiprazole is administered twice daily on days 8-14, about 1 mg brexpiprazole is administered twice daily on days 15-21, and about 1-1.5 mg brexpiprazole is administered once daily starting on day 22. In some embodiments, about 0.5 mg brexpiprazole is administered twice daily on days 1-7 of brexpiprazole treatment, about 1 mg brexpiprazole is administered twice daily on days 8-14, about 1-1.5 mg brexpiprazole is administered twice daily on days 15-21, and about 1-1.5 mg brexpiprazole is administered once daily starting on day 22.

In some embodiments, the patient with MDD in an obese patient who is not a CYP2D6 poor metabolizer (in other words, the patient is an obese CYP2D6 EM patient), and the method comprises: (a) administering either 0.5 or 1 mg brexpiprazole twice daily on each of the first 7 days of brexpiprazole treatment; (b) administering double the individual brexpiprazole dose of step (a) once daily on each of the next 7 days following step (a); and then (c) administering the recommended daily dose of brexpiprazole (e.g., 2-3 mg/day) once daily thereafter. In some embodiments, the patient with MDD is an obese patient who is a CYP2D6 poor metabolizer (i.e., an obese CYP2D6 PM), and the method comprises: (a) administering 0.5 mg brexpiprazole twice daily on each of the first 7 days of brexpiprazole treatment; (b) administering 1 mg twice daily on each of the next 7 days following step (a); and then (c) administering half of the recommended daily dose of brexpiprazole (1-1.5 mg/day) once daily thereafter. In some embodiments, the patient with MDD is an obese patient who is a CYP2D6 poor metabolizer (i.e., an obese CYP2D6 PM), and the method comprises (a) administering 0.25 mg brexpiprazole twice daily on each of the first 7 days of brexpiprazole treatment; (b) administering 0.5 twice daily on each of next 7 days following step (a); (c) administering 1 mg daily twice on each of the next 7 days following step (b); and then (d) administering half of the recommended daily dose of brexpiprazole (1-1.5 mg/day) once daily thereafter;

In some embodiments, an obese CYP2D6 EM or obese CYP2D6 PM patient with MDD is treated with a modified dosage regimen as found in Table 4. The dosage found in Table 4 is the total daily dose of brexpiprazole. Where indicated, the total daily dose is divided into two doses.

TABLE 4

Dosing Regimens for MDD

| Dosage Regimen | Days 1-7 | Days 8-14 | Days 15+ | Weight | CYP2D6 Status |
|---|---|---|---|---|---|
| FDA Label | 0.5 mg (QD) | 1 mg (QD) | 2-3 mg (QD) | All | EM |
| FDA Label | 1 mg (QD) | 2 mg (QD) | 2-3 mg (QD) | All | EM |
| FDA Label | 0.25 mg (QD) | 0.5 mg (QD) | 1-1.5 mg (QD) | All | PM |
| FDA Label | 0.5 mg (QD) | 1 mg (QD) | 1-1.5 mg (QD) | All | PM |
| Modified Dosing Regimen A | 0.5 mg (BID) | 1 mg (QD) | 2-3 mg (QD) | Obese | EM |
| Modified Dosing Regimen B | 1 mg (BID) | 2 mg (QD) | 2-3 mg (QD) | Obese | EM |
| Modified Dosing Regimen C | 0.25 mg (BID) | 0.5 mg (BID) | 1 mg (BID to 21 days) 1-1.5 mg (QD starting on day 22) | Obese | PM |
| Modified Dosing Regimen D | 0.5 mg (BID) | 1 mg (BID) | 1-1.5 mg (QD) | Obese | PM |
| Modified Dosing Regimen E | 0.25 mg (BID) | 1 mg (QD) | 1-1.5 mg (QD) | Normal-weight | PM |
| Modified Dosing Regimen F | 0.5 mg (BID) | 1 mg (QD) | 1-1.5 mg (QD) | Normal-weight | PM |

Patient Populations

Applicants have found that certain classes of patients, i.e., obese patients and/or poor hepatic enzyme metabolizers (e.g., CYP2D6 PM), treated with brexpiprazole according to the instructions within the brexpiprazole FDA label (revised March 2020), have substantially lower plasma levels of brexpiprazole when initiating treatment with brexpiprazole, exhibit a substantially longer elimination half-lives (t½) of brexpiprazole compared to those exhibited in "normal" patients, and have lower $C_{min}$ values than those exhibited in "normal" patients. "Normal" patients are patients who do not exhibit the specific physiological characteristics described herein such as BMI of at least about 35 kg/m², % IBW of at least about 150%, waist size greater than about 42 inches, % body fat greater than about 40%, % android body fat greater than about 40%, % gynoid body fat greater than about 40%, total body fat greater than about 40 kg, optionally in combination with impaired hepatic metabolizing enzyme function, e.g., intermediate or poor CYP2D6 metabolizers. Initiating brexpiprazole treatment according to the methods of the disclosure raises the plasma levels of brexpiprazole more quickly to therapeutic levels, and thus increases the $C_{min}$ values of brexpiprazole more rapidly to the therapeutic levels obtained by normal patients dosed according to the regimen described in the FDA-approved labels for brexpiprazole published prior to the present invention (e.g., the REXULTI® label dated March 2020).

In some embodiments, the methods of the disclosure are used to treat a patient that is obese. In some embodiments, an obese patient has various characteristics of body fat status (BFS). The term "body fat status," "body fat characteristics," "obese status," "obese characteristics," "body habitus," or other derivations or variations thereof refer to at least seven characteristics (BMI, % IBW, waist size, % body fat, % android fat, % gynoid fat, and total body fat) as described herein. In some embodiments, an obese patient can be classified using one or more of the aforementioned BFS. In some embodiments, obese patients exhibit one or more of the following characteristics: BMI of at least about 35 kg/m², % IBW of at least about 150%, waist size greater than about 42 inches, % body fat greater than about 40%, % android body fat greater than about 40%, % gynoid body fat greater than about 40%, total body fat greater than about 40 kg.

In some embodiments, the class of patients treated by the methods of the present disclosure have a body mass index (BMI; expressed in units of kg/m² unless otherwise specified) of at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, at least about 100, at least about 101, at least about 102, at least about 103, at least about 104, at least about 105, at least about 106, at least about 107, at least about 108, at least about 109, at least about 110, at least about 111, at least about 112, at least about 113, at least about 114, at least about 115, at least about 116, at least about 117, at least about 118, at least about 119, at least about 120, at least about 121, at least about 122, at least about 123, at least about 124, at least about 125, at least about 126, at least about 127, at least about 128, at least about 129, at least about 130, at least about 131, at least about 132, at least about 133, at least about 134, at least about 135, at least about 136, at least about 137, at least about 138, at least about 139, at least about 140, at least about 141, at least about 142, at least about 143, at least about 144, at least about 145, at least about 146, at least about 147, at least about 148, at least about 149, at least about 150, at least about 151, at least about 152, at least about 153, at least about 154, at least about 155, at least about 156, at least about 157, at least about 158, at least about 159, at least about 160, at least about 161, at least about 162, at least about 163, at least about 164, at least about 165, at least about 166, at least about 167, at least about 168, at least about 169, at least about 170, at least about 171, at least about 172, at least about 173, at least about 174, at least about 175, at least about 176, at least about 177, at least about 178, at least about 179, at least about 180, at least about 181, at least about 182, at least about 183, at least about 184, at least about 185, at least about 186, at least about 187, at least about 188, at least about 189, at least about 190, at least about 191, at least about 192, at least about 193, at least about 194, at least about 195, at least about 195, at least about 196, at least about 197, at least about 198, at least about 199, at least about 200, at least about 201, at least about 202, at least about 203, at least about 204, at least about 205, at least about 206, at least about 207, at least about 208, at least about 209, or at least about 210, inclusive of all ranges and subranges therebetween, and any BMI described herein. In one embodiment, the patient has a body mass index (BMI) of at least about 35. In another embodiment, the patient has a body mass index (BMI) of at least about 40. In another embodiment, the patient has a body mass index (BMI) of at least 50.

In some embodiments, a patient treated according to the methods of the present invention has a BMI of at least about 25 to at least about 29.9, at least about 25.5 to at least about 29, at least about 26 to at least about 28.5, at least about 26.5 to at least about 28, or at least about 27 to at least about 27.5, inclusive of all ranges and subranges therebetween, and can be termed overweight or pre-obese. In some embodiments, a patient with a BMI of at least about 30 to at least about 34.9, at least about 30.5 to at least about 34, at least about 31 to at least about 33.5, at least about 31.5 to at least about 33, or at least about 32 to at least about 32.5, inclusive of all ranges and subranges therebetween can be considered obese. In some embodiments, a patient with a BMI of at least about 35 to at least about 39.9, at least about 35.5 to at least about 39, at least about 36 to at least about 38.5, at least about 36.5 to at least about 38, or at least about 37 to at least about 37.5, inclusive of all ranges and subranges therebetween, and any BMI described herein, can be considered obese. In other embodiments, a patient treated by the methods of the present disclosure has a BMI of at least about 35 or more, 40 or more, 50 or more, 60 or more, 70 or more, 80 or more, 90 or more, 100 or more, 110 or more, 120 or more, 130 or more, 140 or more, 150 or more, 160 or more, 170 or more, 180 or more, 190 or more, 200 or more, or 210 or more, inclusive of all ranges and subranges therebetween.

In some embodiments, the patient treated according to the methods of the present disclosure is a child or an adolescent with a BMI of at least about the 85th percentile to at least about 95th percentile, at least about the 86th percentile to at least about 94th percentile, at least about the 87th percentile to at least about 93th percentile, at least about the 88th percentile to at least about 92th percentile, at least about the 89th percentile to at least about 90th percentile, inclusive of all ranges and subranges therebetween, can be considered overweight or pre-obese. In some embodiments, the patient is a patient with a BMI of at least about the 95th percentile, at least about 96th percentile, at least about the 97th percentile, at least about 98th percentile, at least about 99th percentile, or at least about 100th percentile, inclusive of all ranges and subranges therebetween, and any BMI percentile described herein, and can be considered obese. In one embodiment, the patient is about 5 to about 19 years old or about 7 to about 18 years old.

In some embodiments, the patient treated according to the methods of the present disclosure is a female patient in the first trimester through third trimester of a pregnancy and has a BMI of at least 25 to at least about 29.9, at least about 25.5 to at least about 29, at least about 26 to at least about 28.5, at least about 26.5 to at least about 28, or at least about 27 to at least about 27.5, inclusive of all ranges and subranges therebetween, and can be considered overweight or pre-obese. In some embodiments, the patient is a female patient in the first trimester through third trimester of a pregnancy and has a BMI of at least about 30 to at least about 34.9, at least about 30.5 to at least about 34, at least about 31 to at least about 33.5, at least about 31.5 to at least about 33, or at least about 32 to at least about 32.5, inclusive of all ranges and subranges therebetween, and can be considered obese. In some embodiments, the patent treated according to the methods of the present invention is a female patient in the first trimester through third trimester of a pregnancy and has a BMI of at least about 35 to at least about 39.9, at least about 35.5 to at least about 39, at least about 36 to at least about 38.5, at least about 36.5 to at least about 38, at least about 37 to at least about 37.5, inclusive of all ranges and subranges therebetween, and can be considered severely obese.

In some embodiments, methods of calculating BMI may include, but are not limited to body weight in kilogram/(height in meters)$^2$, body weight in pounds/(height in inches)$^2$]×703, and the like.

In some embodiments, the patient treated according to the methods of the present disclosure can alternatively be described as having a % ideal body weight (% ibw) of at least about 110%, at least about 111%, at least about 112%, at least about 113%, at least about 114%, at least about 115%, at least about 116%, at least about 117%, at least about 118%, at least about 119%, at least about 120%, at least about 121%, at least about 122%, at least about 123%, at least about 124%, at least about 125%, at least about 126%, at least about 127%, at least about 128%, at least about 129%, at least about 130%, at least about 131%, at least about 132%, at least about 133%, at least about 134%, at least about 135%, at least about 136%, at least about 137%, at least about 138%, at least about 139%, at least about 140%, at least about 141%, at least about 142%, at least about 143%, at least about 144%, at least about 145%, at least about 146%, at least about 147%, at least about 148%, at least about 149%, at least about 150%, at least about 151%, at least about 152%, at least about 153%, at least about 154%, at least about 155%, at least about 156%, at least about 157%, at least about 158%, at least about 159%, at least about 160%, at least about 161%, at least about 162%, at least about 163%, at least about 164%, at least about 165%, at least about 166%, at least about 167%, at least about 168%, at least about 169%, at least about 170%, at least about 171%, at least about 172%, at least about 173%, at least about 174%, at least about 175%, at least about 176%, at least about 177%, at least about 178%, at least about 179%, at least about 180%, at least about 181%, at least about 182%, at least about 183%, at least about 184%, at least about 185%, at least about 186%, at least about 187%, at least about 188%, at least about 189%, at least about 190%, at least about 191%, at least about 192%, at least about 193%, at least about 194%, at least about 195%, at least about 196%, at least about 197%, at least about 198%, at least about 199%, at least about 200%, at least about 201%, at least about 202%, at least about 203%, at least about 204%, at least about 205%, at least about 206%, at least about 207%, at least about 208%, at least about 209%, at least about 210%, at least about 211%, at least about 212%, at least about 213%, at least about 214%, at least about 215%, at least about 216%, at least about 217%, at least about 218%, at least about 219%, at least about 220%, at least about 221%, at least about 222%, at least about 223%, at least about 224%, at least about 225%, at least about 226%, at least about 227%, at least about 228%, at least about 229%, at least about 230%, at least about 231%, at least about 232%, at least about 233%, at least about 234%, at least about 235%, at least about 236%, at least about 237%, at least about 238%, at least about 239%, at least about 240%, at least about 241%, at least about 242%, at least about 243%, at least about 244%, at least about 245%, at least about 246%, at least about 247%, at least about 248%, at least about 249%, at least about 250%, at least about 251%, at least about 252%, at least about 253%, at least about 254%, at least about 255%, at least about 256%, at least about 257%, at least about 258%, at least about 259%, at least about 260%, at least about 261%, at least about 262%, at least about 263%, at least about 264%, at least about 265%, at least about 266%, at least about 267%, at least about 268%, at least about 269%, at least about 270%, at least about 271%, at least about 272%, at least about 273%, at least about 274%, at least about 275%, at least about 276%, at least about 277%, at least about 278%, at least about 279%, or at least about 280%, inclusive of all ranges and subranges therebetween, and any % ideal body weight described herein. In one embodiment, the patient has % ideal body weight (IBW) of at least about 150%. In one embodiment, the patient has % ideal body weight (IBW) of at least about 250%. In other embodiment, the patient has % IBW of at least 150% and can be considered obese.

In some embodiments, the patient treated according to the present disclosure can alternatively be described as having a waist size or waist circumference greater than about 32, greater than about 33, greater than about 34, greater than about 35 inches, greater than about 36, greater than about 37, greater than about 38, greater than about 39, greater than about 40, greater than about 41, greater than about 42, greater than about 43, greater than about 44, greater than about 45, greater than about 46, greater than about 47, greater than about 48, greater than about 49, greater than about 50, greater than about 51, greater than about 52, greater than about 53, greater than about 54, greater than about 55, greater than about 56, greater than about 57, greater than about 58, greater than about 59, greater than about 60 inches, greater than about 61 inches, greater than about 62 inches, greater than about 63 inches, greater than about 64 inches, greater than about 65 inches, inclusive of all ranges and subranges therebetween, and any waist size or circumference described herein. In one embodiment, a patient having a waist size or waist circumference of about 42 inches can be considered obese. In another embodiment, the patient has waist size or waist circumference greater than about 48 inches. In other embodiment, the patient has waist or waist circumference of at least 42 inches.

In some embodiments, a patient treated according to the methods of the present disclosure has a % body fat greater than about 20%, greater than about 21%, greater than about 22%, greater than about 23%, greater than about 24%, greater than about 25%, greater than about 26%, greater than about 27%, greater than about 28%, greater than about 29%, greater than about 30%, greater than about 31%, greater than about 32%, greater than about 33%, greater than about 34%, greater than about 35%, greater than about 36%, greater than about 37%, greater than about 38%, greater than about 39%, greater than about 40%, greater than about 41%, greater than about 42%, greater than about 43%, greater than about 44%, greater than about 45%, greater than about 46%, greater than about 47%, greater than about 48%, greater than about 49%, or greater than about 50%, inclusive of all ranges and subranges therebetween, and any % body fat described herein. In one embodiment, the patient has a % body fat greater than about 40%. In one embodiment, the patient has a % body fat of at least about 50%. In another embodiment, a patient having a % body fat greater than about 40% can be considered obese. In some embodiments, methods of calculating % body fat can include, but are not limited to total body fat expressed as a percentage of total body weight. Other standards for obesity can be used. For example, the American Council on Exercise suggests that an "average" percentage of body fat for women is about 25-31%, and for men, about 18-24%, and for obese women, about 32% and higher, and obese men, about 25% and higher.

In some embodiments, a patient treated according to the methods of the present disclosure has a % android body fat greater than about 30%, greater than about 31%, greater than about 32%, greater than about 33%, greater than about 34%, greater than about 35%, greater than about 36%, greater than about 37%, greater than about 38%, greater than about 39%, greater than about 40%, greater than about 41%, greater than about 42%, greater than about 43%, greater than about 44%, greater than about 45%, greater than about 46%, greater than about 47%, greater than about 48%, greater than about 49%, greater than about 50%, greater than about 51%, greater than about 52%, greater than about 53%, greater than about 54%, greater than about 55%, greater than about 56%, greater than about 57%, greater than about 58%, greater than about 59%, greater than about 60%, greater than about 61%, greater than about 62%, greater than about 63%, greater than about 64%, greater than about 65%, greater than about 66%, greater than about 67%, greater than about 68%, greater than about 69%, greater than about 70%, greater than about 71%, greater than about 72%, greater than about 73%, greater than about 74%, greater than about 75%, greater than about 76%, greater than about 77%, greater than about 78%, greater than about 79%, or greater than about 80%, inclusive of all ranges and subranges therebetween, and any % android body fat described herein. In one embodiment, a patient having a % android body fat greater than about 40% can be considered obese. In one embodiment, a patient having a % android body fat greater than about 50% can be considered obese.

In some embodiments, a patient treated according to the methods of the present disclosure has a % android body fat of at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, or at least about 80%, inclusive of all ranges and subranges therebetween, and % android body fat described herein. In one embodiment, the patient has % android body fat of at least about 50%.

In some embodiments, a patient treated according to the methods of the present disclosure has a % gynoid body fat greater than about 30%, greater than about 31%, greater than about 32%, greater than about 33%, greater than about 34%, greater than about 35%, greater than about 36%, greater than about 37%, greater than about 38%, greater than about 39%, greater than about 40%, greater than about 41%, greater than about 42%, greater than about 43%, greater than about 44%, greater than about 45%, greater than about 46%, greater than about 47%, greater than about 48%, greater than about 49%, greater than about 50%, greater than about 51%, greater than about 52%, greater than about 53%, greater than about 54%, greater than about 55%, greater than about 56%, greater than about 57%, greater than about 58%, greater than about 59%, greater than about 60%, greater than about 61%, greater than about 62%, greater than about 63%, greater than about 64%, greater than about 65%, greater than about 66%, greater than about 67%, greater than about 68%, greater than about 69%, greater than about 70%, greater than about 71%, greater than about 72%, greater than about 73%, greater than about 74%, greater than about 75%, greater than about 76%, greater than about 77%, greater than about 78%, greater than about 79%, or greater than about 80%, inclusive of all ranges and subranges therebetween, and any % gynoid body fat described herein. In one embodiment, a patient having a % gynoid body fat greater than about 40% can be considered obese. In one embodiment, a patient having a % gynoid body fat greater than about 50% can be considered obese.

In some embodiments, a patient treated according to the methods of the present disclosure has a total body fat content greater than about 30 kg, greater than about 31 kg, greater than about 32 kg, greater than about 33 kg, greater than about 34 kg, greater than about 35 kg, greater than about 36 kg, greater than about 37 kg, greater than about 38 kg, greater than about 39 kg, greater than about 40 kg, greater than about 41 kg, greater than about 42 kg, greater than about 43 kg, greater than about 44 kg, greater than about 45 kg, greater than about 46 kg, greater than about 47 kg, greater than about 48 kg, greater than about 49 kg, greater than about 50 kg, greater than about 51 kg, greater than about 52 kg, greater than about 53 kg, greater than about 54 kg, greater than about 55 kg, greater than about 56 kg, greater than about 57 kg, greater than about 58 kg, greater than about 59 kg, greater than about 60 kg, greater than about 61 kg, greater than about 62 kg, greater than about 63 kg, greater than about 64 kg, greater than about 65 kg, greater than about 66 kg, greater than about 67 kg, greater than about 68 kg, greater than about 69 kg, greater than about 70 kg, greater than about 71 kg, greater than about 72 kg, greater than about 73 kg, greater than about 74 kg, greater than about 75 kg, greater than about 76 kg, greater than about 77 kg, greater than about 78 kg, greater than about 79 kg, greater than about 80 kg, greater than about 81 kg, greater than about 82 kg, greater than about 83 kg, greater than about 84 kg, greater than about 85 kg, greater than about 86 kg, greater than about 87 kg, greater than about 88 kg, greater than about 89 kg, greater than about 90 kg, greater than about 91 kg, greater than about 92 kg, greater than about 93 kg, greater than about 94 kg, greater than about 95 kg, greater than about 96 kg, greater than about 97 kg, greater than about 98 kg, greater than about 99 kg, greater than about 100 kg, at least 101 kg, at least 102 kg, at least 103 kg, at least 104 kg, at least 105 kg, at least 106 kg, at least 107 kg, at least 108 kg, at least 109 kg, or at least 110 kg, inclusive of all ranges and subranges therebetween, and any total body fat described herein. In one embodiment, a patient having total body fat greater than about 40 kg can be considered obese. In one embodiment, a patient having total body fat greater than about 50 kg can be considered obese.

In other embodiments, obesity status of patients treated with the methods of the present disclosure can be measured by waist-to-hip ratio. In other embodiments, obesity status of patients can be measured by skinfold thickness. In other embodiments, obesity status of patients can be measured by bioelectric impedance. In other embodiments, obesity status of patients can be measured by underwater weighing or densitometry. In other embodiments, the obesity status of patients can be measured by air-displacement plethysmography. In other embodiments, obesity status of patients can be measured by dilution method or hydrometry. In other embodiments, the obesity status of patients can be measured by dual energy X-ray absorptiometry. In other embodiments, the obesity status of patients can be measured by computerized tomography and magnetic resonance imaging. In some embodiments, the obesity status can be defined by, but is not limited to adopting the clinical standards, conventional standards, and/or the standards published by the World Health Organization and Center of Disease Control (both of which are herein incorporated by reference in their entireties for all purposes) when using the methods described herein. For example, the WHO defines an obese person as a person with a BMI of 30 or more, an overweight person is one with a BMI equal to or more than 25 (to less than 30). Similarly, the CDC defines normal as a BMI of 18.5 to less than 25, 25.0 to less than 30 as overweight, and 30.0 or higher as obese. The CDC further subdivides obesity into 3 classes: Class 1, a BMI of 30 to less than 35; Class 2, a BMI of 35 to less than 40; and Class 3, as a BMI of 40 or higher. The CDC sometimes refers to Class 3 obesity as "extreme" or "severe" obesity.

As used herein, the term "about" refers to an amount somewhat more or less than the stated parameter value, for example plus or minus five or ten percent of the object that "about" modifies, or as one of skill in the art would recognize from the context (e.g., approximately 50% of the interval between values). The term "about" also includes the value referenced. For example, a BMI of about 40 includes 40, as well as values somewhat below or above 40.

In some embodiments, the patient treated by the methods of the present disclosure can be characterized by two or more of the physiological characteristics described herein. For example the patient can have a BMI of at least about 35 and can have a % IBW of at least 150%. In some embodiments, the patient can have a BMI of at least about 35 and can have a waist size greater than about 42 inches. In some embodiments, the patient can have a BMI of at least about 35 and can have a % body fat greater than about 40%. In some embodiments, the patient can have a BMI of at least about 35 and can have a % android body fat greater than about 40%. In some embodiments, the patient can have a BMI of at least about 35 and can have a % gynoid body fat greater than about 40%. In some embodiments, the patient can have a BMI of at least about 35 and can have total body fat greater than about 40 kg. In various other embodiments, the patient can have any combination of two or more of any of the specific physiological parameters described herein.

In some embodiments, the patient can have three or more of the physiological parameters described herein, for example a BMI of at least about 35, a % IBW of at least 150%, and waist size greater than about 42 inches. In some embodiments, the patient can have a BMI of at least about 35, a % IBW of at least 150%, and a % body fat greater than about 40%. In some embodiments, the patient can have a BMI of at least about 35, a % IBW of at least 150%, and a % android body fat greater than about 40%. In some embodiments, the patient can have a BMI of at least about 35, a % IBW of at least 150%, and a % gynoid body fat greater than about 40%. In some embodiments, the patient can have a BMI of at least about 35, a % IBW of at least 150%, and total body fat greater than about 40 kg. In various other embodiments, the patient can have any combination of three or more of any of the specific physiological parameters described herein.

In some embodiments, the patient can have four or more of the physiological parameters described herein, for example the patient can have a BMI of at least about 35, a % IBW of at least 150%, waist size greater than about 42 inches, and a % body fat greater than about 40%. In some embodiments, the patient can have a BMI of at least about 35, a % IBW of at least 150%, waist size greater than about 42 inches, and a % android body fat greater than about 40%. In some embodiments, the patient can have a BMI of at least about 35, a % IBW of at least 150%, waist size greater than about 42 inches, and a % gynoid body fat greater than about 40%. In some embodiments, the patient can have a BMI of at least about 35, a % IBW of at least 150%, a waist size greater than about 42 inches, and total body fat greater than about 43 kg. In some embodiments, the patient can have a BMI of at least about 35, a % IBW of at least 150%, a waist size greater than about 42 inches, a % body fat greater than about 40%, and a % android body fat greater than about 40%. In some embodiments, the patient can have a BMI of at least about 35, a % IBW of at least 150%, a waist size greater than about 42 inches, a % body fat greater than about 40%, and a % gynoid body fat greater than about 40%. In some embodiments, the patient can have a BMI of at least about 35, a % IBW of at least 150%, a waist size greater than about 42 inches, a % body fat greater than about 40%, and total body fat greater than about 40 kg. In some embodiments, the patient can have a BMI of at least about 35, a % IBW of at least 150%, a waist size greater than about 42 inches, a % body fat greater than about 40%, a % android body fat greater than about 40%, in % gynoid body fat greater than about 40%, and total body fat greater than about 40 kg. In one embodiment, the patient who has a BMI of at least about 35, in % IBW of at least 150%, a waist size greater than about 42 inches, and a % body fat greater than about 40%, a % android body fat greater than about 40%, a % gynoid body fat greater than about 40%, and total body fat greater than about 40 kg. In various other embodiments, the patient can have any combination of any or all of the specific physiological parameters described herein.

In some embodiments, the patient can have a waist size greater than about 42 inches, a % body fat greater than about 40%, and a % android body fat greater than about 40%. In some embodiments, the patient can have a waist size greater than about 42 inches, a % body fat greater than about 40%, and a % gynoid body fat greater than about 40%. In some embodiments, the patient can have a waist size greater than about 42 inches, a % body fat greater than about 40%, and total body fat greater than about 40 kg.

In some embodiments, the patient can have a % body fat greater than about 40%, a % android body fat greater than about 40%, and a % gynoid body fat greater than about 40%. In some embodiments, the patient can have a % body fat greater than about 40%, a % android body fat greater than about 40%, and total body fat greater than about 40 kg. In some embodiments, the patient can have a % body fat greater than about 40%, a % gynoid body fat greater than about 40%, and total body fat greater than about 40 kg. In some embodiments, a % android body fat greater than about 40%, and a % gynoid body fat greater than about 40%, and total body fat greater than about 43 kg. In some embodiments, the patient can have any combinations of obesity characteristics described herein.

In some embodiments, the methods of the disclosure are used to treat a normal-weight patient. As used herein, a normal-weight patient has a BMI between about 18 kg/m$^2$ and 25 kg/m$^2$. In some embodiments, normal-weight patients do not exhibit one or more of the following characteristics: BMI of at least about 35 kg/m$^2$, % IBW of at least about 150%, waist size greater than about 42 inches, % body fat greater than about 40%, % android body fat greater than about 40%, % gynoid body fat greater than about 40%, total body fat greater than about 40 kg.

In some embodiments, the patient treated by the methods of the present disclosure can be an adult human. In other embodiments, the patient can be a male human. In still other embodiments, the patient can be a female human.

In some embodiments, the methods of the disclosure are utilized to treat patients with various hepatic enzyme statuses. Brexpiprazole is metabolized primarily through oxidation via P450 isozymes such as CYP2D6. Alternatively, brexpiprazole is metabolized through oxidation via P450 isozymes such as CYP3A4/5, CYP2C9, CYP2C19, CYP2A6, CYP2C8, or CYP2B6. Each individual may have different activity levels of the P450 isozymes to metabolize brexpiprazole. Categorizations of metabolizers may include, but are not limited to allelic heterogeneity in the P450 isozyme genes. For instance, the CYP2D6 gene can have allelic heterogeneity and its functionality (i.e., associated enzyme activity) can be categorized as full functionality, decreased functionality, and non-functionality. Further, CYP2D6 genotype can be categorized based on its metabolic status by using the "gene dose" method and can have the following scoring scale: (1) alleles with full functionality: a value of 1, (2) alleles with reduced functionality: a value of 0.5, and (3) alleles with no functionality: a value of 0. Alternatively, in some embodiments, the CYP2D6 genotype can be tested by using targeted variant analysis. In some embodiments, the CYP2D6 genotype can be tested by using sequence analysis of select exons.

The "normal" or typical patient has 2 normally functioning CYP2D6 alleles, and has full "normal" CYP2D6 enzyme functionality or activity and is referred to as an "extensive CYP2D6 metabolizer." Patients with one non-functional CYP2D6 allele and one normally functioning allele have reduced CYP2D6 enzyme function and are termed "intermediate CYP2D6 metabolizers." Patients with 2 non-functional CYP2D6 alleles have little or no CYP2D6 functionality or activity and are termed "poor CYP2D6 metabolizers" or alternatively "CYP2D6 poor metabolizers (PM)."

As used herein, the term "extensive CYP2D6 metabolizer" refers to a person who may have a gene dose score for the CYP2D6 allele of 1.5 or 2 and may have superior capabilities for metabolizing brexpiprazole compared to his or her counterpart who is assigned as "intermediate CYP2D6 metabolizer" or "poor CYP2D6 metabolizer." As used herein, the term "intermediate CYP2D6 metabolizer" refers to a person who may have a gene dose score for the CYP2D6 allele of 0.5 to 1 and may have superior capabilities for metabolizing brexpiprazole compared to his or her counterpart who is assigned as "poor CYP2D6 metabolizer." As used herein, the term "poor CYP2D6 metabolizer" refers to a person who may have a gene dose score for the CYP2D6 allele of 0 and may have the least capabilities for metabolizing brexpiprazole compared to his or her counterpart who is assigned as an "intermediate metabolizer" or an "extensive metabolizer." In some embodiments, other suitable or conventional standards of categorizing CYP2D6 metabolizers may be used.

In some embodiments, the methods of the disclosure are used to treat a CYP2D6 poor metabolizer. In some embodiments, the methods of the disclosure are used to treat a CYP2D6 extensive metabolizer. In some embodiments, the methods of the disclosure are used to treat a CYP2D6 intermediate metabolizer.

In some embodiments, the methods of the disclosure are used to treat a patient that is an intermediate CYP2D6 metabolizer and has at least one of the obesity characteristics described herein. In some embodiments, the methods of the disclosure are used to treat a patient that is a poor CYP2D6 metabolizer and has at least one of the obesity characteristics described herein. In some embodiments, the methods of the disclosure are used to treat a patient that is an extensive CYP2D6 metabolizer and has at least one of the obesity characteristics described herein.

In some embodiments, the methods of the disclosure are utilized to treat a patient that is a normal weight and is an intermediate CYP2D6 metabolizer. In some embodiments, the methods of the disclosure are utilized to treat a patient that is a normal weight and is a poor CYP2D6 metabolizer. In some embodiments, the methods of the disclosure are utilized to treat a patient that is a normal weight and is an extensive CYP2D6 metabolizer.

In some embodiments, the methods of the disclosure are utilized to treat a patient that has a BMI greater than 25 kg/m$^2$ but less than 35 kg/m$^2$ and is an intermediate CYP2D6 metabolizer. In some embodiments, the methods of the disclosure are utilized to treat a patient that has a BMI greater than 25 kg/m$^2$ but less than 35 kg/m$^2$ and is a poor CYP2D6 metabolizer. In some embodiments, the methods of the disclosure are utilized to treat a patient that has a BMI greater than 25 kg/m$^2$ but less than 35 kg/m$^2$ and is an extensive CYP2D6 metabolizer.

In some embodiments, the methods of the disclosure are used to treat a patient with a disease selected from major depressive disorder, schizophrenia, post-traumatic stress disorder, bipolar disorder, bipolar depression, acute mania, agitation associated with Alzheimer's disease, borderline personality disorder, attention deficit hyperactivity disorder, autism, conduct disorder, oppositional defiant disorder, and combinations thereof.

In some embodiments, the methods of the disclosure are used to treat a patient with major depressive disorder. In some embodiments, the methods of the disclosure are used as an adjunctive therapy to treat a patient with major depressive disorder. In some embodiments, the methods of the disclosure are used to treat a patient with schizophrenia.

As used herein, "normal," "normal-weight," "reference," or other derivations or variations thereof refers to a non-obese state in a person who can have at least one of the following characteristics: BMI less than about 35 kg/m², % IBW less than about 150%, waist size less than about 42, % body fat less than about 40%, % android body fat less than about 40%, % gynoid body fat less than about 40%, and total body fat less than about 40 kg. Unless otherwise modified "normal metabolizer" also means an extensive CYP2D6 metabolizer.

Pharmacokinetics

In some embodiments, after administering between about 0.5 mg and about 8 mg (e.g., 0.25 mg, 0.5 mg, 1.0 mg, 2.0 mg, 2.5 mg, 3.0 mg, 3.5 mg, 4.0 mg, 5.0 mg, 6.0 mg, 7.5 mg, 8 mg) of brexpiprazole, the obese CYP2D6 PM or obese CYP2D6 EM patient treating according to the modified dosing regimens disclosed herein have a minimum observed plasma drug concentration ($C_{min}$) between about 30 ng/mL and about 120 ng/mL. In some embodiments, the $C_{min}$ is between about 30 ng/mL and about 60 ng/mL nine days after administration of the day 1 dose of brexpiprazole. In some embodiments, the $C_{min}$ is between about 60 ng/mL and about 95 ng/mL 16 days after administration of the day 1 dose of brexpiprazole. In some embodiments, the $C_{min}$ is at least about 40.4 ng/mL. In some embodiments, the $C_{min}$ is at least about 90.9 ng/mL. In some embodiments, the $C_{min}$ is at least about 10.1 ng/mL. In some embodiments, the $C_{min}$ is at least about 40.4 ng/mL on day 14 of brexpiprazole administration. In some embodiments, the $C_{min}$ is at least about 90.9 ng/mL on day 14 of brexpiprazole administration. In some embodiments, the $C_{min}$ is at least about 10.1 ng/mL on day 14 of brexpiprazole administration. In some embodiments, the $C_{min}$ is about 30 ng/mL, about 35 ng/mL, about 40 ng/mL, about 45 ng/mL, about 50 ng/mL, about 55 ng/mL, about 60 ng/mL, about 65 mg/mL, about 70 ng/mL, about 75 ng/mL, about 80 ng/mL, about 85 ng/mL, about 90 ng/mL, about 95 ng/mL, about 100 ng/mL, about 105 ng/mL, about 110 ng/mL, about 115 ng/mL, about 120 ng/mL, about 125 ng/mL, or about 130 ng/mL, including all ranges and values in between. In some embodiments, the $C_{min}$ is between 80% and 125% of any of the aforementioned values or ranges between the aforementioned values.

In some embodiments, the time to reach Cmin is reduced after dosage of brexpiprazole according to a modified dosage regimen described herein as compared to dosage according to the brexpiprazole (REXULTI®) FDA label dated March 2020. Example 2 shows that the time to reach therapeutic concentrations of brexpiprazole using the modified dosage regimen is reduced in the patient populations described herein as compared to the time to reach Cmin using the brexpiprazole (REXULTI®) FDA Label. In some embodiments, the time to reach Cmin according to a modified dosage regimen is reduced by between about 1 day and about 35 days, for example, at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 2 days, 21 days, 22 days, 23 days, 24 days, 25 days, 26 days, 27 days, 28 days, 29 days, 30 days, 31 days, 32 days, 33 days, 34 days, or at least about 35 days, including all values and ranges there between as compared to dosage according to the brexpiprazole (REXULTI®) FDA label.

In some embodiments, after administering between about 0.5 mg and about 8 mg (e.g., 0.25 mg, 0.5 mg, 1.0 mg, 2.0 mg, 2.5 mg, 3.0 mg, 3.5 mg, 4.0 mg, 5.0 mg, 6.0 mg, 7.5 mg, 8 mg) of brexpiprazole, the obese CYP2D6 PM patient or obese CYP2D6 EM patient has a maximum observed plasma drug concentration ($C_{max}$) between about 50 ng/mL and about 150 ng/mL. In some embodiments, the $C_{max}$ is between about 50 ng/mL and about 100 ng/mL nine days after administration of the day 1 dose of brexpiprazole. In some embodiments, the $C_{max}$ is between about 80 ng/mL and about 150 ng/mL 16 days after administration of the day 1 dose of brexpiprazole. In some embodiments, the $C_{max}$ is about 50 ng/mL, about 55 ng/mL, about 60 ng/mL, about 65 mg/mL, about 70 ng/mL, about 75 ng/mL, about 80 ng/mL, about 85 ng/mL, about 90 ng/mL, about 95 ng/mL, about 100 ng/mL, about 105 ng/mL, about 110 ng/mL, about 115 ng/mL, about 120 ng/mL, about 125 ng/mL, about 130 ng/mL, about 135 ng/mL, about 140 ng/mL, about 145 ng/mL, or about 150 ng/mL including all ranges and values in between. In some embodiments, the $C_{max}$ is between 80% and 125% of any of the aforementioned values or ranges between the aforementioned values.

In some embodiments, after administering between about 0.25 mg and about 8 mg (e.g., 0.25 mg, 0.5 mg, 1.0 mg, 2.0 mg, 2.5 mg, 3.0 mg, 3.5 mg, 4.0 mg, 5.0 mg, 6.0 mg, 7.5 mg, 8 mg) of brexpiprazole, the obese CYP2D6 PM or obese CYP2D6 EM patient has an area under the concentration time curve from day 0 to day 9 ($AUC_9$) between 1000 ng*hr/mL and 2000 ng*hr/mL. In some embodiments, after administering between about 0.5 mg and about 10 mg, the patient has an $AUC_9$ of between 1500 ng*hr/mL and 2000 ng*hr/mL. In some embodiments, the $AUC_9$ is about 1000 ng*hr/mL, about 1100 ng*hr/mL, about 1200 ng*hr/mL, about 1300 ng*hr/mL, about 1400 ng*hr/mL, about 1500 ng*hr/mL, about 1600 ng*hr/mL, about 1700 ng*hr/mL, about 1800 ng*hr/mL, about 1900 ng*hr/mL, or about 2000 ng*hr/mL, including all ranges and values in between. In some embodiments, the $AUC_9$ is between 80% and 125% of the aforementioned values.

In some embodiments, after administering between about 0.25 mg and about 8 mg (e.g., 0.25 mg, 0.5 mg, 1.0 mg, 2.0 mg, 2.5 mg, 3.0 mg, 3.5 mg, 4.0 mg, 5.0 mg, 6.0 mg, 7.5 mg, 8 mg) of brexpiprazole, the obese CYP2D6 PM patient or obese CYP2D6 EM patient has an area under the concentration time curve from day 0 to day 16 ($AUC_{16}$) between 1800 ng*hr/mL and 2600 ng*hr/mL. In some embodiments, after administering between about 0.5 mg and about 10 mg, the patient has an $AUC_{16}$ between 2000 ng*hr/mL and 2600 ng*hr/mL. In some embodiments, after administering between about 0.5 mg and about 10 mg, the patient has an $AUC_{16}$ between 2000 ng*hr/mL and 2300 ng*hr/mL. In some embodiments, the $AUC_{16}$ is about about 1800 ng*hr/mL, about 1900 ng*hr/mL, about 2000 ng*hr/mL, about 2100 ng*hr/mL, about 2200 ng*hr/mL, about 2300 ng*hr/mL, about 2400 ng*hr/mL, about 2500 ng*hr/mL, or about 2600 ng*hr/mL, including all ranges and values in between. In some embodiments, the $AUC_{16}$ is between 80% and 125% of the aforementioned values.

All documents or patents cited herein are incorporated by reference in their entireties for all purposes.

The following examples are offered by way of illustration and not by way of limitation.

Example 1. Brexpiprazole Pharmacokinetics in Obese and Obese CYP2D6 PM

Brexpiprazole is an atypical antipsychotic indicated to treat schizophrenia and for use as an adjunctive therapy to antidepressants for the treatment of major depressive disorder. Brexpiprazole is known to have a drug-drug interaction with CYP2D6 inhibitors, and dose reductions are recommended for patients that are cytochrome P450 CYP2D6 poor metabolizers (PM) or patients taking concomitant CYP2D6 inhibitors. CYP2D6 EM patients metabolize brexpiprazole normally, whereas CYP2D6 PM patients are believed to eliminate brexpiprazole more slowly. The FDA label of brexpiprazole (REXULTI®) advises that these patient populations take half of the usual dose of brexpiprazole. Table A shows the recommended dosing schedule of brexpiprazole for treating schizophrenia in patients that are CYP2D6 PM and CYP2D6 extensive metabolizers (EM). The brexpiprazole FDA label does not contain recommendations for brexpiprazole dosage according to body size. Therefore, obese patients (as described herein) are treated according to the same dosing schedule as EM or PM (depending on their CYP2D6 metabolizer status)

TABLE A

Brexpiprazole Dosing for Schizophrenia According to FDA Label

| CYP2D6 | Days 1-4 | Days 5-7 | Days 8+ |
|---|---|---|---|
| EM | 1 mg QD | 2 mg QD | 2-4 mg QD |
| PM | 0.5 mg QD | 1 mg QD | 1-2 mg QD |

PBPK Modeling of Patients Dosed with Brexpiprazole According to the FDA Label

Physiologically based pharmacokinetic (PBPK) modeling was used to estimate the pharmacokinetic parameters of brexpiprazole of the following schizophrenia patient populations after administering brexpiprazole according to the FDA label (REXULTI® label dated March 2020): obese (BMI>35 kg/m$^2$), normal weight (BMI=18 kg/m$^2$-25 kg/m$^2$), CYP2D6 poor metabolizer (PM), and CYP2D6 extensive metabolizer (EM). Although the PBPK modeling was based on the dosing regimen for schizophrenia according to the FDA label (REXULTI®, March 2020), pharmacokinetic parameters are dose-dependent and expected to be similar in MDD.

In order to simulate brexpiprazole under various conditions, a whole-body PBPK model was constructed to capture the drug's kinetics in major tissues. Model tissue compartments included adipose, bone, brain, large intestine, small intestine, heart, kidney, liver, lung, muscle, spleen, stomach, and skin tissues, as well as venous and arterial blood compartments. In order to accurately capture first-pass clearance effects on the drug, the model also included correct representation of the gastrointestinal tract organs and the liver. Additionally, a peripheral sampling site compartment was used to represent the PK-sampled venous blood concentration as it was found to more accurately capture referenced plasma concentrations. Drug distribution into each tissue compartment was modeled assuming perfusion-limited kinetics, with partitioning into tissue described by a partition coefficient (Kp) estimated using methods described by Poulin and Theil (2002). Brexpiprazole-specific biochemical parameters such as the log of octanol:water partition coefficient (log P), negative log acid dissociation constant (pKa), fraction unbound in the plasma ($f_{up}$), blood:plasma concentration ratio (BP), and clearance were obtained from literature; additional physiochemical properties used to calculate Kps were obtained via DrugBank. Absorption was modeled assuming simple first-order absorption, and clearance of brexpiprazole was assumed to occur entirely in the liver (~1% renal clearance). Based on the literature it was assumed that 46.7% of brexpiprazole clearance is due to CYP3A4, with the remaining clearance due to CYP2D6 (43.3%) and other routes (10%). The impact of CYP2D6 PM status is known to decrease baseline clearance by ~30%, which was reflected in the reduced baseline clearance parameters due to CYP2D6 in PM simulations. Simulations were carried out in a virtual population of 500 normal-weight and 500 obese individuals with age- and sex-specific physiological parameters (i.e. tissue flows and volumes) sampled from the National Health and Nutrition Examination Survey (NHANES) dataset.

Model parameters were calibrated and subsequently qualified by digitizing PK data from available literature and comparing predicted vs. observed $AUC_{0-\infty}$, $C_{max}$, and time to $C_{max}$ ($T_{max}$) under various dose strengths, dosing scenarios (i.e., single dose vs. multiple dose), and routes of administration (i.e., intravenous or oral formulations). Calibration and qualification simulations were carried out using a single typical individual (male, age=30 years, weight=73 kg, and height=1.76 m). All comparisons yielded a geometric mean fold error less than or equal to 2, and thus were considered accurate for these purposes.

The Applicant's model was validated and shown to accurately predict observed and literature pharmacokinetic parameters as shown in Tables B and C, below.

TABLE B

| | | | Model Validation | | | | | | | | |
|---|---|---|---|---|---|---|---|---|---|---|---|
| | | | AUC (ng · h/mL) | | | Cmax (ng/mL) | | | Tmax (h) | | |
| Reference | Route | Dose (mg) | Observed | Predicted | GMFE | Observed | Predicted | GMFE | Observed | Predicted | GMFE | Calibration |
| NDA | IV | 0.25 | 172 | 175 | 1.02 | 4.73 | 5.07 | 1.07 | 1 | 1 | 1.0 | Yes |
| Study1 | PO | 2 | 1690 | 1350 | 1.25 | 22.10 | 19.5 | 1.13 | 6 | 4 | 1.5 | Yes |
| NDA | PO | 0.2 | 123 | 135 | 1.10 | 2.62 | 1.95 | 1.35 | 2 | 4 | 2.0 | No |
| Study2 | PO | 0.5 | 287 | 337 | 1.17 | 6.64 | 4.87 | 1.36 | 4 | 4 | 1.0 | No |
| | PO | 1 | 636 | 675 | 1.06 | 11.70 | 9.74 | 1.20 | 6 | 4 | 1.5 | No |
| | PO | 2 | 2160 | 1350 | 1.60 | 24.60 | 19.50 | 1.27 | 4 | 4 | 1.0 | No |
| | PO | 4 | 2760 | 2700 | 2.00 | 47.20 | 38.90 | 1.21 | 6 | 4 | 1.5 | No |
| | PO | 6 | 5230 | 4050 | 1.29 | 71.10 | 58.40 | 1.22 | 6 | 4 | 1.5 | No |
| | PO | 8 | 7920 | 5400 | 1.47 | 79.20 | 77.90 | 1.02 | 6 | 4 | 1.5 | No |

GMFE = geometric mean fold error
Calibration: Data used to optimize and/or refine PK parameters in the final model
References are from NDA 205422 Clinical Pharmacology and Biopharmaceutics Review, p. 26 and 28

TABLE C

Comparison to Literature CYP2D6 PM PK Values
Brexpiprazole Model Comparisons

| Cohort | Dose | AUC Normal | AUC Obese | AUC GMR Expected | AUC GMR Normal | AUC GMR Obese | % Expected GMR Normal | % Expected GMR Obese |
|---|---|---|---|---|---|---|---|---|
| CYP2D6 EM | 4 mg | 2703 | 2779 | 1.0 | 1.00 | 1.00 | 100% | 100% |
| CYP2D6 PM | 4 mg | 4289 | 4397 | 1.5 | 1.59 | 1.58 | 106% | 105% |
| CYP2D6 PM | 2 mg | 2134 | 2093 | 0.75 | 0.79 | 0.75 | 105% | 100% |

Figure 2A:
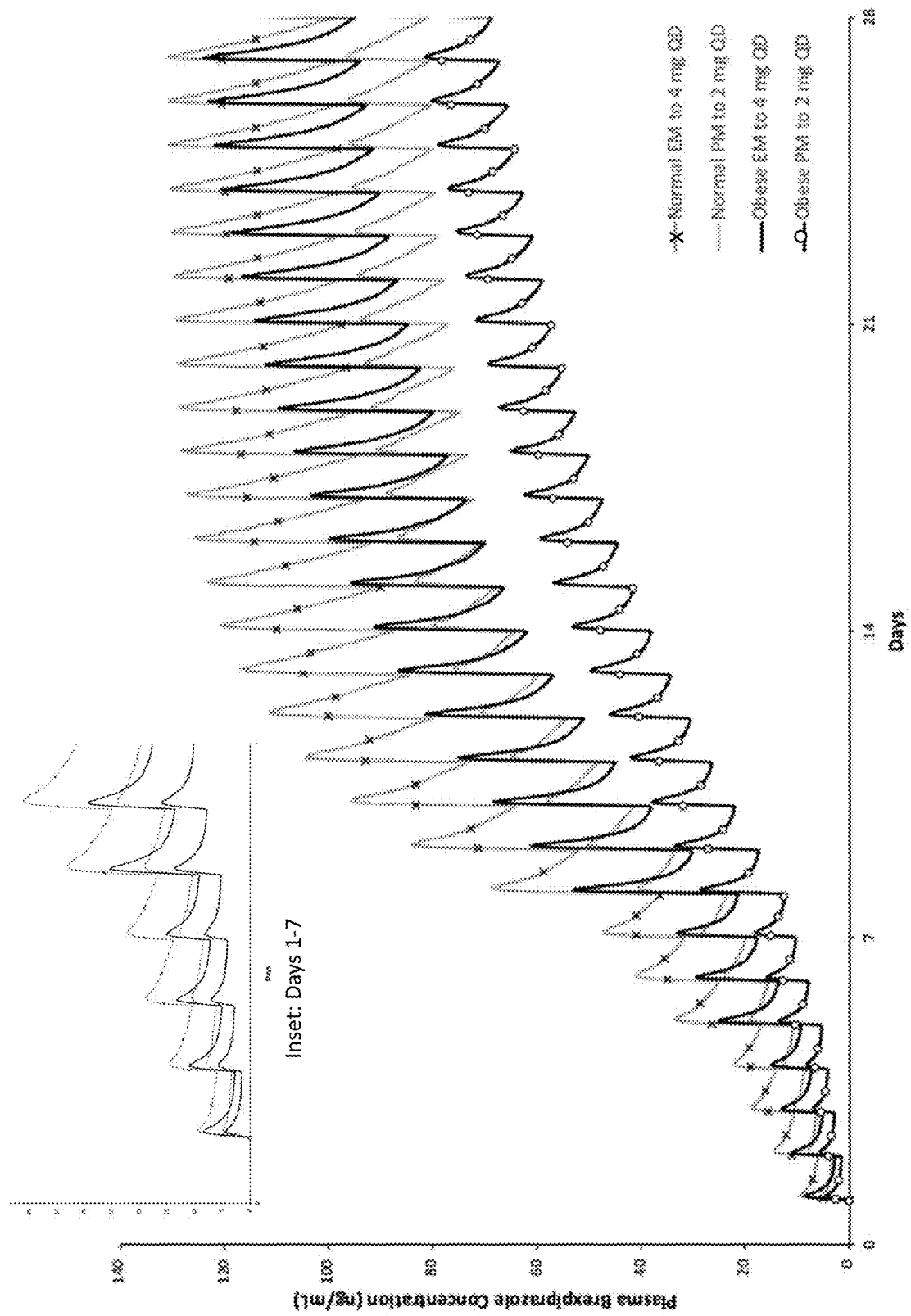
FIG. 2A shows the plasma levels of brexpiprazole in normal-weight CYP2D6 EM, normal-weight CYP2D6 PM, obese CYP2D6 EM, and obese CYP2D6 PM patients with schizophrenia that are treated according to the brexpiprazole FDA label. Obese CYP2D6 EM and obese CYP2D6 PM patients take longer to reach therapeutic concentrations of brexpiprazole than normal-weight CYP2D6 EM patients, and may not reach therapeutic concentrations at all in the first 28 days of brexpiprazole administration.
Figure 2B:
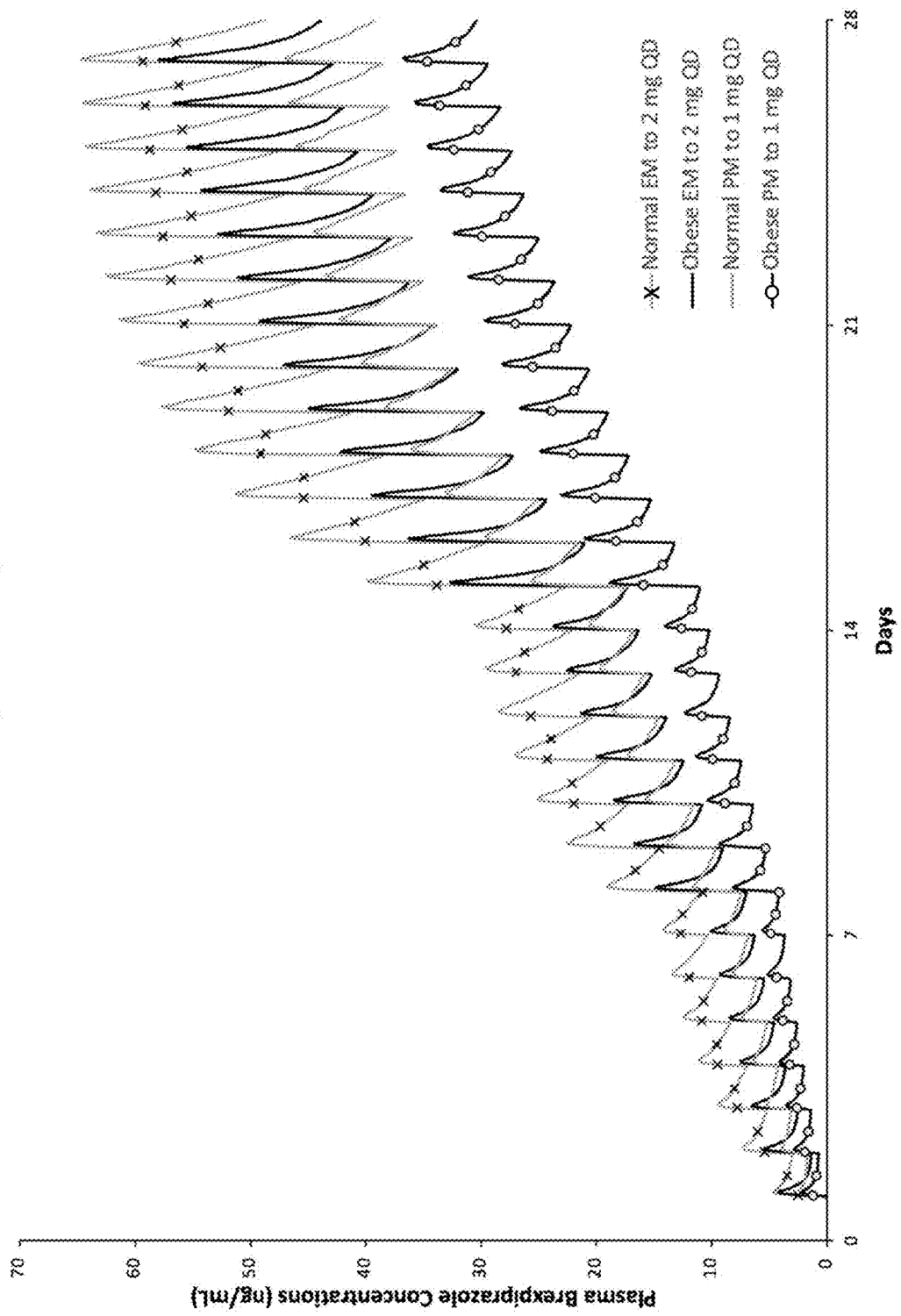
FIG. 2B shows the plasma levels of brexpiprazole in normal-weight CYP2D6 EM, normal-weight CYP2D6 PM, obese CYP2D6 EM, and obese CYP2D6 PM patients with MDD that are treated according to the brexpiprazole FDA label, with a starting dose of 0.5 mg. Obese CYP2D6 EM and obese CYP2D6 PM patients take longer to reach therapeutic concentrations of brexpiprazole than normal-weight CYP2D6 EM patients, and may not reach therapeutic concentrations at all in the first 28 days of brexpiprazole administration.

"Expected" values are based on population PK analysis in NDA 205422 Clinical Pharmacology and Biopharmaceutics Review The modeling data showed that patients that are obese and obese CYP2D6 PM take significantly longer to reach therapeutic plasma levels of brexpiprazole when initiating brexpiprazole treatment (Table D, and FIG. 2A). This is based, at least in part, on Applicant's surprising discovery that the half-life of brexpiprazole is dependent on both body size and CYP2D6 metabolizer status. Normal-weight CYP2D6 EM exhibit a lower mean half-life than patients that are obese and/or CYP2D6 PM (Table D).

TABLE D

Half-Life of Brexpiprazole in Different Patient Populations

| Weight | CYP2D6 | Mean half-life (SD), hours |
|---|---|---|
| Normal | EM | 68.6 (45.0) |
| Obese | EM | 192 (130) |
| Normal | PM | 107 (71.3) |
| Obese | PM | 297 (207) |

Additionally, obese and obese CYP2D6 PM patients take longer to reach steady state plasma levels and therapeutic concentrations compared to normal weight CYP2D6 EM when dosed using the instructions on the FDA label (Table E where EC50, EC80, and EC90 correspond to the plasma concentration at with 50%, 80%, or 90% of the population is expected to respond to treatment, respectively). Consequently, these patients take significantly longer to be treated than previously known, and some patients may not actually reach therapeutic brexpiprazole concentrations. Thus, obese and CYP2D6 PM schizophrenia patients dosed according to the FDA label (e.g., REXULTI® label dated March 2020) are not effectively treated. Ineffective schizophrenia treatment results in severe complications, including suicide attempts, anxiety, depression, alcohol or drug abuse, inability to work or attend school, financial problems, homelessness, social isolation, health and medical problems, being victimized, and aggressive behavior.

TABLE E

Pharmacokinetics Based on Current FDA Label

| | | Days to Reach Pharmacokinetic Endpoints | | |
|---|---|---|---|---|
| Weight | CYP2D6 | EC50 | EC80 | Steady State |
| Normal | EM | 3 | 9 | 21 |
| Obese | EM | 6 | 11 | 37 |
| Normal | PM | 5 | 10 | 24 |
| Obese | PM | 7 | 15 | 46 |

Example 2. Schizophrenia

PBPK Modeling of Schizophrenia Patients Treated with Higher Doses According to Modified Methods A modified dosing regimen was developed so that obese and CYP2D6 PM patients reach therapeutic levels earlier (Table F). The modified dosage regimen for obese CYP2D6 EM and normal-weight CYP2D6 PM comprises doubling the total daily dose of brexpiprazole for days 1-7 of the dosage regimen. On day 8, patients returned to administering the recommended dose once daily. The modified dosage regimen for obese CYP2D6 PM comprises doubling the total daily dose of brexpiprazole for days 1-14 of the dosage regimen. On day 15, patients returned to administering the recommended dose once daily. In contrast to the modified dosage regimen for obese CYP2D6 PM described herein which doubles the total daily brexpiprazole dosage for days 1-14, the brexpiprazole FDA label recommends decreasing the total daily brexpiprazole dosage by one-half in these patients.

TABLE F

Modified Schizophrenia Dosing Regimens

| Weight | CYP2D6 | Days 1-4 | Days 5-7 | Days 8-14 | Days 15+ |
|---|---|---|---|---|---|
| All (Label) | EM | 1 mg QD (1 mg total daily dose) | 2 mg QD (2 mg total daily dose) | 4 mg QD (4 mg total daily dose) | 4 mg QD (4 mg total daily dose) |
| Obese (Modified Dosing Regimen 1) | EM | 1 mg BID (2 mg total daily dose) | 2 mg BID (4 mg total daily dose) | 4 mg QD (4 mg total daily dose) | 4 mg QD (4 mg total daily dose) |
| All (Label) | PM | 0.5 mg QD (0.5 mg total daily dose) | 1 mg QD (1 mg total daily dose) | 2 mg QD (2 mg total daily dose) | 2 mg QD (2 mg total daily dose) |
| Obese (Modified Dosing Regimen 2) | PM | 0.5 mg BID (1 mg total daily dose) | 1 mg BID (2 mg total daily dose) | 2 mg BID (4 mg total daily dose) | 2 mg QD (2 mg total daily dose) |
| Weight | CYP2D6 | Days 1-4 | Days 5-7 | Days 8-14 | Days 15+ |
| Non-Obese (Modified Dosing Regimen 3) | PM | 0.5 mg BID (1 mg total daily dose) | 1 mg BID (2 mg total daily dose) | 1-2 mg (QD) | 1-2 mg (QD) |

PBPK modeling shows that the pharmacokinetic parameters of obese CYP2D6 PM and obese CYP2D6 EM schizophrenia patients treated with the modified dosage regimen of Table F approach those of normal-weight CYP2D6 EM (Table I).

FIG. 3 shows that obese CYP2D6 EM schizophrenia patients that are treated according to Modified Dosing Regimen 1 have plasma brexpiprazole concentrations that are similar to normal-weight CYP2D6 EM patients. Obese CYP2D6 EM patients that are administered twice the starting and recommended daily doses for the first 7 days reach therapeutic concentrations three days faster than obese CYP2D6 EM patients that are administered brexpiprazole according to the FDA label (Table H).

FIG. 4 shows that obese CYP2D6 PM schizophrenia patients that are treated according to Modified Dosing Regimen 2 reach therapeutic concentration in a similar time to normal-weight CYP2D6 EM patients. Obese CYP2D6 PM schizophrenia patients that are administered brexpiprazole at twice the starting and recommended daily doses for the first 14 days reach therapeutic brexpiprazole concentrations five days faster than once daily dosing (Table H).

FIG. 5 shows that normal-weight CYP2D6 PM schizophrenia patients that are administered brexpiprazole according to Modified Dosing Regimen 3 reach therapeutic concentrations three days faster than once daily dosing.

TABLE G

Days to Reach Pharmacokinetic Endpoints using Modified Brexpiprazole Dosing Regimens of Table F

| Weight | CYP2D6 | Days of BID dosing | EC50 | EC80 | Steady State |
|---|---|---|---|---|---|
| Normal | EM | 0 | 3 | 9 | 21 |
| Obese | EM | 7 | 3 | 8 | 33 |
| Normal | PM | 7 | 3 | 7 | 21 |
| Obese | PM | 14 | 5 | 10 | 17 |

TABLE H

Days Reduced to Reach Pharmacokinetic Endpoints After Dosing According to Modified Dosing Regimen of Table F

| Weight | CYP2D6 | EC50 | EC80 | Steady State |
|---|---|---|---|---|
| Obese | EM | 3 | 3 | −4 |
| Obese | PM | 2 | 5 | −29 |

TABLE I

| | | Label Dosing | | | | Modified Dosing | | |
|---|---|---|---|---|---|---|---|---|
| | | Normal EM | Normal PM | Obese EM | Obese PM | Normal PM | Obese EM | Obese PM |
| Day 9 | AUC (ng * hr/mL) | 1763 | 1073 | 1063 | 611 | 1554 | 1526 | 1166 |
| | Cmax (ng/mL) | 88.2 | 51.8 | 63.7 | 34.7 | 73.4 | 83.3 | 58.1 |
| | Cmin (ng/mL) | 51.9 | 33.2 | 30.0 | 17.3 | 54.4 | 50.2 | 36.5 |
| Day 16 | AUC (ng * hr/mL) | 2600 | 1908 | 1967 | 1229 | 2008 | 2189 | 2147 |
| | Cmax (ng/mL) | 128.8 | 88.4 | 104.1 | 61.2 | 94.0 | 113.7 | 100.2 |
| | Cmin (ng/mL) | 91.8 | 70.3 | 69.9 | 44.4 | 74.8 | 79.6 | 84.0 |

Table G shows that the modified dosage regimen of Table F decreases the time required for schizophrenia patients that are CYP2D6 PM and/or obese to reach therapeutic concentrations. The modified dosage regimen brings the time required for obese CYP2D6 PM, normal-weight CYP2D6 PM, and obese CYP2D6 EM patients to reach therapeutic concentrations closer to that of normal-weight CYP2D6 EM patients.

Table I shows a comparison between the area under the curve, maximal plasma concentration ($C_{max}$), and minimal plasma concentration ($C_{min}$) between schizophrenia patients dosed according to the FDA label and schizophrenia patients dosed according to the modified dosage regimen. The AUC, Cmax, and Cmin for obese CYP2D6 PM, obese CYP2D6 EM, and normal-weight CYP2D6 PM patients approach those of normal-weight CYP2D6 EM patients after treatment with the modified dosing regimen.

Example 3. Major Depressive Disorder (MDD)

PBPK Modeling of MDD Patients Treated with Higher Doses According to Modified Methods A modified dosing regimen was developed so that obese and CYP2D6 PM patients reach therapeutic levels earlier (Table J). For obese CYP2D6 EM, the modified dosage regimen comprises doubling the total daily dose of brexpiprazole for days 1-7 of the dosage regimen on the brexpiprazole label. On day 8, the patients are treated with the recommended dose once daily according to the brexpiprazole label. For obese CYP2D6 PM, the modified dosage regimen comprises doubling the total daily dose of brexpiprazole for days 1-14 or 1-21 (depending on the starting dose) of the dosage regimen. Thereafter (on day 15 or 22, depending on the starting dose), the patients are treated with the recommended dose once daily according to the brexpiprazole label. In contrast to these modified dosage regimens for obese CYP2D6 PM (which doubles the total daily brexpiprazole dosage), the FDA label recommends decreasing the total daily brexpiprazole dosage by one-half in these patients.

TABLE J

Modified MDD Dosing Regimens

| Weight | CYP2D6 | Days 1-7 | Days 8-14 | Days 15-21 | Days 21+ |
|---|---|---|---|---|---|
| All (FDA Label) | EM | 0.5 mg QD (0.5 mg total daily dose) | 1 mg QD (1 mg total daily dose) | 2 mg QD (2 mg total daily dose) | 2-3 mg QD (2-3 mg total daily dose) |
| All (FDA Label) | EM | 1.0 mg QD (1.0 mg total daily dose) | 2 mg QD (2 mg total daily dose) | 2-3 mg QD (2-3 mg total daily dose) | 2-3 mg QD (2-3 mg total daily dose) |
| All (FDA Label) | PM | 0.25 mg QD (0.25 mg total daily dose) | 0.5 mg QD (0.5 mg total daily dose) | 1.0 mg QD (1.0 mg total daily dose) | 1-1.5 mg QD (1-1.5 mg total daily dose) |
| All (FDA Label) | PM | 0.5 mg QD (0.5 mg total daily dose) | 1 mg QD (1 mg total daily dose) | 1-1.5 mg QD (2 mg total daily dose) | 1-1.5 mg QD (1-1.5 mg total daily dose) |
| Obese (Modified Dosing Regimen A) | EM | 0.5 mg BID (1 mg total daily dose) | 1 mg QD (1 mg total daily dose) | 2 mg QD (2 mg total daily dose) | 2-3 mg QD (2-3 mg total daily dose) |
| Obese (Modified Dosing Regimen B) | EM | 1 mg BID (2 mg total daily dose) | 2 mg QD (2 mg total daily dose) | 2-3 mg QD (2 mg total daily dose) | 2-3 mg QD (2-3 mg total daily dose) |
| Obese (Modified Dosing Regimen C) | PM | 0.25 mg BID (0.5 mg total daily dose) | 0.5 mg BID (1 mg total daily dose) | 1 mg BID (2 mg total daily dose) | 1 mg QD |
| Obese (Modified Dosing Regimen D) | PM | 0.5 mg BID (1 mg total daily dose) | 1 mg BID (2 mg total daily dose) | 1 mg QD | 1 mg QD |
| Normal (Modified Dosing Regimen E) | PM | 0.25 mg BID (0.5 mg total daily dose) | 0.5 mg QD | 1 mg QD | 1-1.5 mg QD |
| Normal (Modified Dosing Regimen F) | PM | 0.5 mg BID (1 mg total daily dose) | 1 mg QD | 1-1.5 mg QD | 1-1.5 mg QD |

PBPK modeling shows that the pharmacokinetic parameters of obese CYP2D6 PM and obese CYP2D6 EM schizophrenia patients treated with the modified dosage regimen of Table J approach those of normal-weight CYP2D6 EM (Table K and Table L).

FIG. 6 shows the blood plasma profiles for obese CYP2D6 EM patients with MDD that are treated according to Modified Dosing Regimen A, and FIG. 7 shows blood plasma profiles for obese patient that are treated according to Modified Dosing Regimen B. In both FIG. 6 and FIG. 7, starting on day 8, the recommended dose was administered once daily.

FIG. 6 shows that obese CYP2D6 EM MDD patients that are treated according to the Modified Dosing Regimen A (BID for the first 7 days and return to the recommended dose thereafter) have plasma brexpiprazole concentrations that are similar to normal-weight CYP2D6 EM patients.

FIG. 7 shows that obese CYP2D6 EM MDD patients that are treated according to the Modified Dosing Regimen B (BID for the first 7 days and return to the recommended dose thereafter) have plasma brexpiprazole concentrations that are similar to normal-weight CYP2D6 EM patients.

Figure 8:
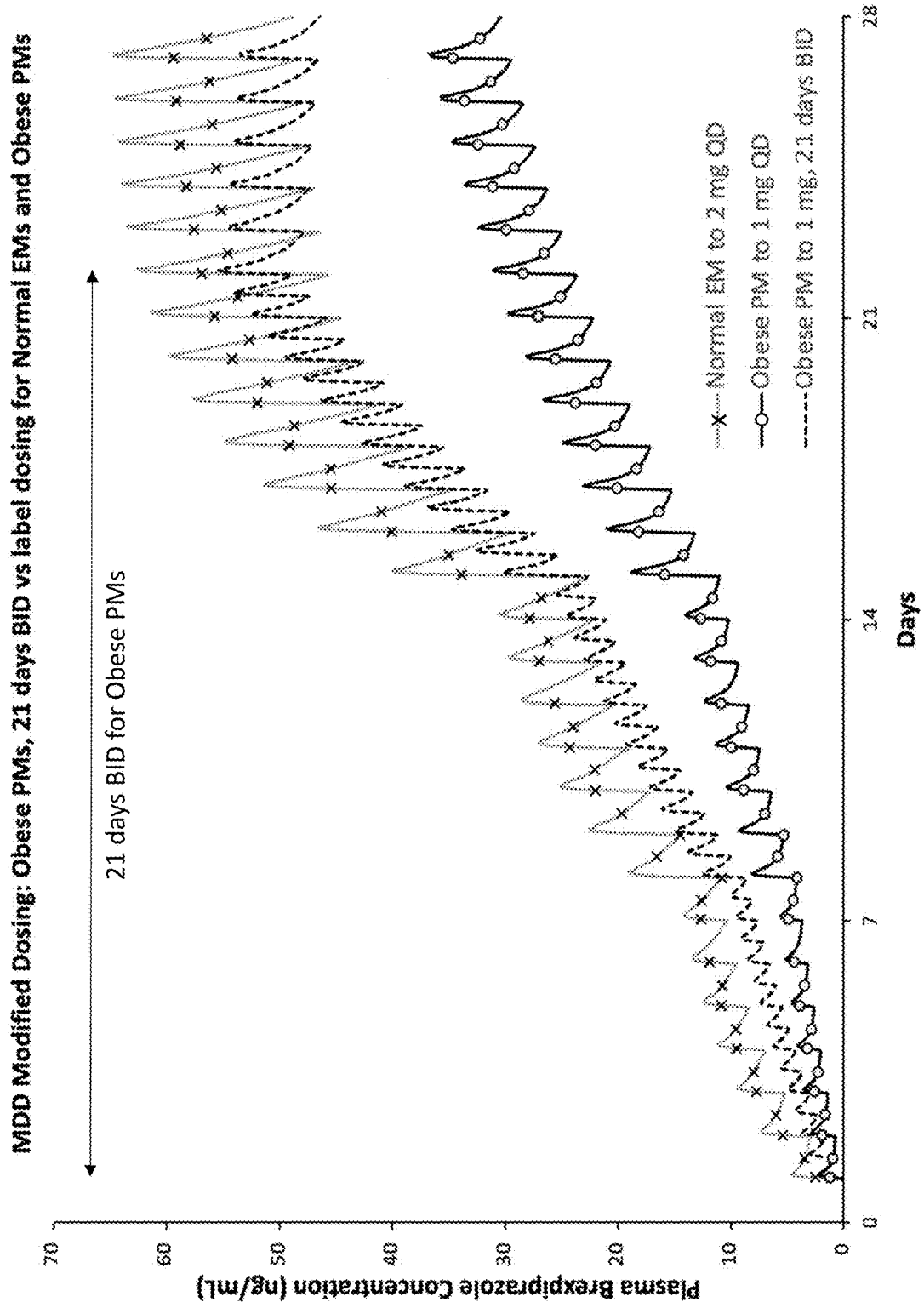
FIG. 8 shows the plasma levels of brexpiprazole over time of obese CYP2D6 PM major depressive disorder patients that are administered 0.25 mg brexpiprazole twice daily for the first seven days, 0.5 mg twice daily for days 8-15, and 1 mg twice daily for days 16-21 (Table 4. Modified Dosing Regimen C). Obese CYP2D6 PM patients treated according to the disclosed modified dosage regimen reach therapeutic concentrations that are similar to normal-weight CYP2D6 EM patients treated according to the brexpiprazole FDA label. When administered brexpiprazole according to the FDA label, obese CYP2D6 PM patients do not reach therapeutic concentrations in the first 28 days of administration.
Figure 9:
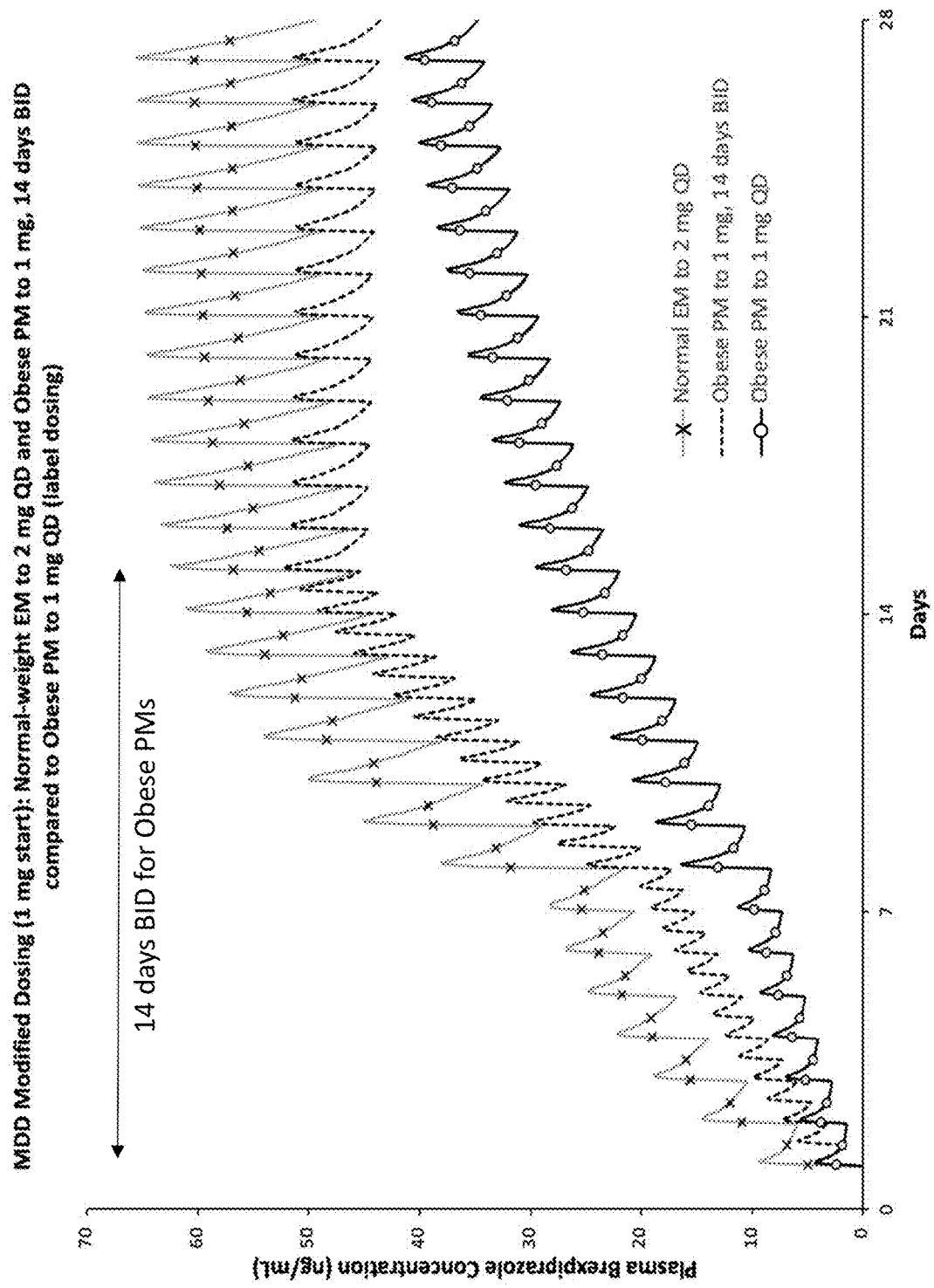
FIG. 9 shows the plasma levels of brexpiprazole over time of obese CYP2D6 PM major depressive disorder patients that are administered 0.5 mg brexpiprazole twice daily for the first 7 days, and 1 mg twice daily on days 8-14 (Table 4. Modified Dosing Regimen D). Obese CYP2D6 PM patients treated according to the modified dosage regimen reach therapeutic concentrations of brexpiprazole in a similar time as normal-weight CYP2D6 EM patients treated according to the brexpiprazole FDA label. When administered brexpiprazole according to the FDA label, obese CYP2D6 PM patients do not reach therapeutic concentrations in the first 28 days of administration.

FIG. 8 shows the blood plasma profiles for obese CYP2D6 PM patients with MDD that are treated according to Modified Dosing Regimen C, and FIG. 9 shows blood plasma profiles for obese patients that are treated according to Modified Dosing Regimen D. In FIG. 8, starting on day 22, half of the recommended dose was administered once daily. In FIG. 9, starting on day 15, half of the recommended dose was administered once daily.

FIG. 8 shows that obese CYP2D6 PM MDD patients that are treated according to Modified Dosing Regimen C (BID for the first 21 days and return to half the recommended dose thereafter) reach therapeutic concentrations in a similar time to normal-weight CYP2D6 EM patients.

FIG. 9 shows that obese CYP2D6 EM MDD patients that are treated according to the Modified Dosing Regimen D (BID for the first 14 days and return to half the recommended dose thereafter) have plasma brexpiprazole concentrations that are similar to normal-weight CYP2D6 EM patients.

Figure 11:
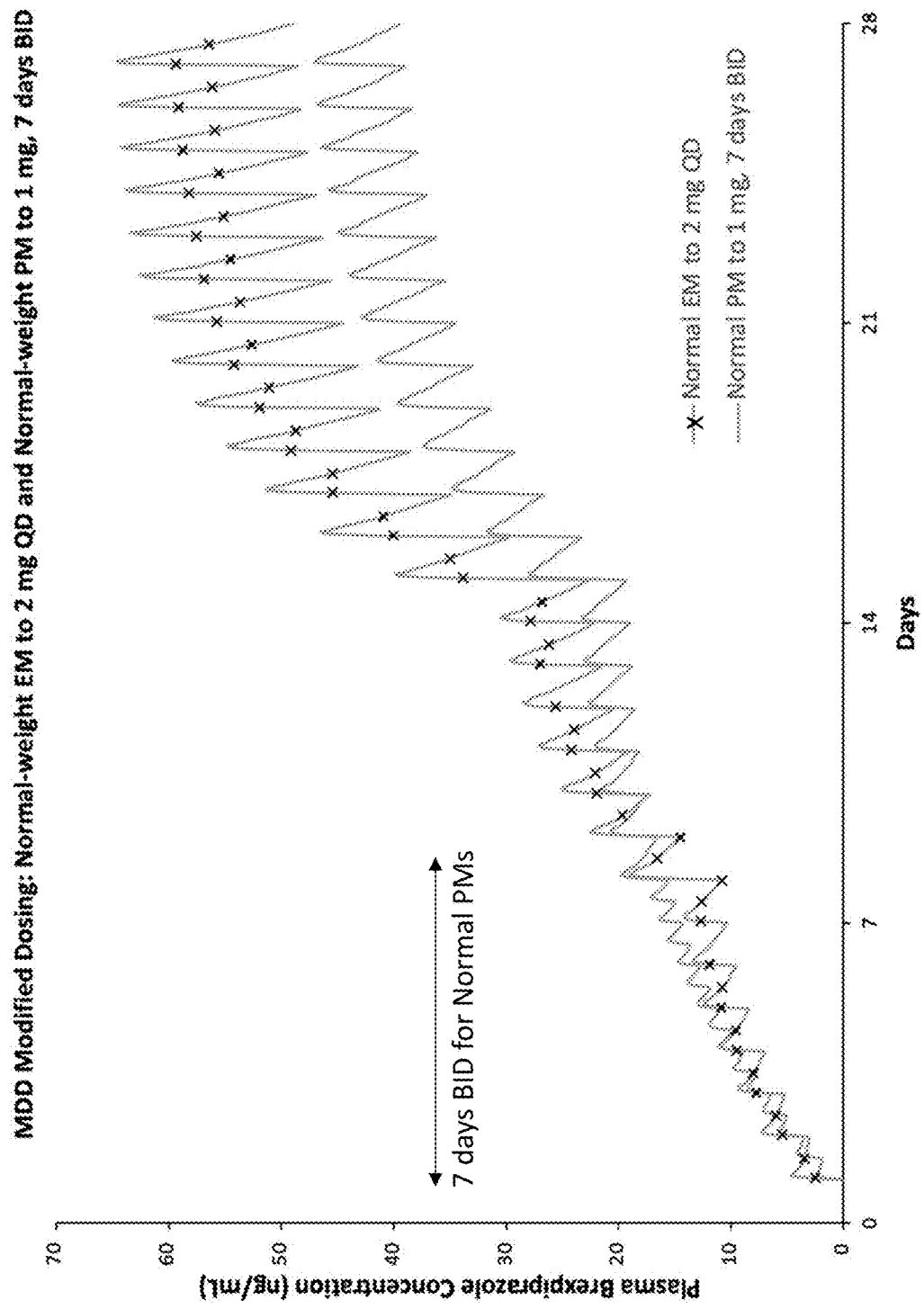
FIG. 11 shows the plasma levels of brexpiprazole over time of normal-weight CYP2D6 PM major depressive disorder patients that are administered 0.25 mg brexpiprazole twice daily for the first 7 days (Table 4. Modified Dosing Regimen E). Normal-weight CYP2D6 PM patients treated according to the modified dosage regimen reach therapeutic concentrations of brexpiprazole in a similar time as normal-weight CYP2D6 EM patients treated according to the brexpiprazole FDA label.
Figure 12:
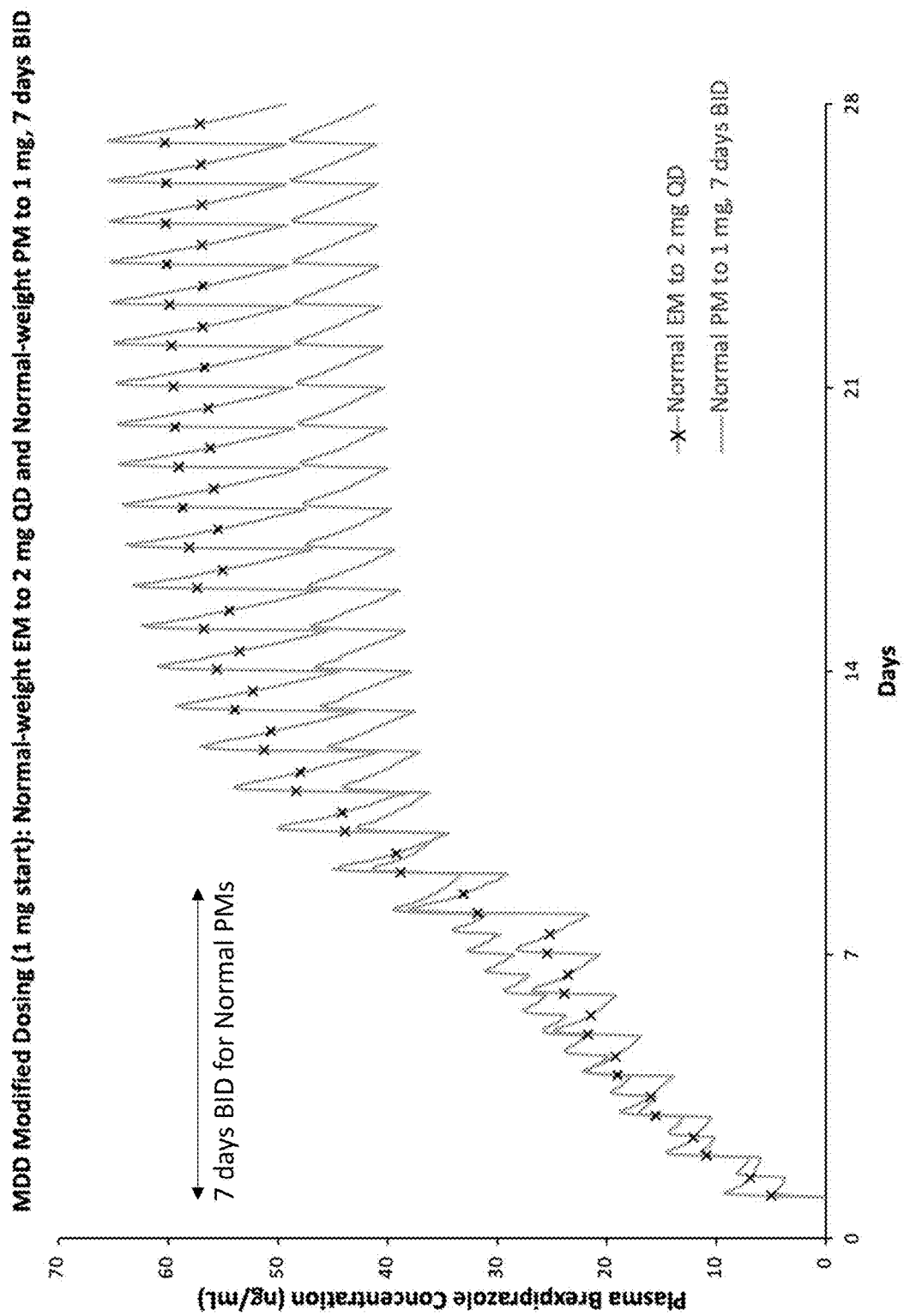
FIG. 12 shows the plasma levels of brexpiprazole over time of normal-weight CYP2D6 PM major depressive disorder patients that are administered 0.5 mg brexpiprazole twice daily for the first 7 days (Table 4. Modified Dosing Regimen F). Normal-weight CYP2D6 PM patients treated according to the modified dosage regimen reach therapeutic concentrations of brexpiprazole in a similar time as normal-weight CYP2D6 EM patients treated according to the brexpiprazole FDA label.

FIG. 11 and FIG. 12 shows that normal-weight CYP2D6 PM MDD patients that are administered brexpiprazole according to Modified Dosing Regimen E and Modified Dosing Regimen F, respectively, reach therapeutic brexpiprazole concentration in a similar time to normal-weight CYP2D6 EM patients.

Table K shows a comparison between the area under the curve, maximal plasma concentration ($C_{max}$), and minimal plasma concentration ($C_{min}$) between MDD patients dosed according to the FDA label and MDD patients dosed according to Modified Dosing Regimens A (starting dose of 0.5 mg BID) and C (starting dose of 0.25 mg BID). The AUC, Cmax, and Cmin for obese CYP2D6 PM, obese CYP2D6 EM, and normal-weight CYP2D6 PM patients approach those of normal-weight CYP2D6 EM patients after treatment with the modified dosing regimen.

TABLE K

Pharmacokinetic Parameters Modified Dosing Regimen with Starting Doses of 0.5 mg BID (Obese CYP2D6 EM) or 0.25 mg BID (Obese CYP2D6 PM)

| | | Label Dosing | | | | Modified Dosing | | |
| --- | --- | --- | --- | --- | --- | --- | --- | --- |
| | | Normal EM | Normal PM | Obese EM | Obese PM | Normal PM | Obese EM | Obese PM |
| Day 21 | AUC (ng * hr/mL) | 1271 | 924 | 965 | 938 | 938 | 1011 | 1209 |
| | Cmax (ng/mL) | 63.3 | 43.1 | 51.4 | 30.6 | 44.0 | 53.3 | 54.8 |
| | Cmin (ng/mL) | 44.5 | 33.8 | 34.2 | 22.2 | 34.5 | 36.0 | 45.9 |
| Day 30 | AUC (ng * hr/mL) | 1368 | 1052 | 1227 | 840 | 1057 | 1246 | 1160 |
| | Cmax (ng/mL) | 66.6 | 48.5 | 62.5 | 40.4 | 48.8 | 63.2 | 54.0 |
| | Cmin (ng/mL) | 49.0 | 39.7 | 45.4 | 32.0 | 39.9 | 6.0 | 45.6 |

Table L shows a comparison between the area under the curve, maximal plasma concentration ($C_{max}$), and minimal plasma concentration ($C_{min}$) between MDD patients dosed according to the FDA label and MDD patients dosed according to Modified Dosing Regimens B (starting dose of 1 mg BID) and D (starting dose of 0.5 mg BID). The AUC, Cmax, and Cmin for obese CYP2D6 PM, obese CYP2D6 EM, and normal-weight CYP2D6 PM patients approach those of normal-weight CYP2D6 EM patients after treatment with the modified dosing regimen.

TABLE L

Pharmacokinetic Parameters Modified Dosing Regimen with Starting Doses of 1 mg BID (Obese CYP2D6 EM) or 0.5 mg BID (Obese CYP2D6 PM)

| | | Label Dosing | | | | Modified Dosing | | |
| --- | --- | --- | --- | --- | --- | --- | --- | --- |
| | | Normal EM | Normal PM | Obese EM | Obese PM | Normal PM | Obese EM | Obese PM |
| Day 21 | AUC (ng * hr/mL) | 1361 | 1031 | 1178 | 776 | 1066 | 1253 | 1121 |
| | Cmax (ng/mL) | 66.4 | 47.7 | 59.9 | 37.7 | 49.2 | 63.5 | 52.2 |
| | Cmin (ng/mL) | 48.7 | 38.8 | 43.1 | 29.3 | 40.3 | 46.5 | 44.2 |
| Day 30 | AUC (ng * hr/mL) | 1375 | 1081 | 1304 | 935 | 1088 | 1332 | 1112 |
| | Cmax (ng/mL) | 66.9 | 49.5 | 65.9 | 44.1 | 49.7 | 67.2 | 52.4 |
| | Cmin (ng/mL) | 49.3 | 40.9 | 48.7 | 35.9 | 41.0 | 50.5 | 43.4 |

The invention claimed is:

1. A method of initiating treatment of schizophrenia with brexpiprazole in an obese patient who is not a CYP2D6 poor metabolizer, comprising:
   (a) administering 1 mg brexpiprazole twice daily on each of the first 4 days of brexpiprazole treatment;
   (b) administering 2 mg brexpiprazole twice daily on each of the next 3 days following step (a); and then
   (c) administering a recommended dose of 2-4 mg/day brexpiprazole once daily thereafter;

wherein the obese patient has one or more of the following characteristics:
   (i) BMI of at least about 35;
   (ii) % IBW of at least about 150%;
   (iii) waist size greater than about 42 inches;
   (iv) % body fat greater than about 40%;
   (v) % android body fat greater than about 40%;
   (vi) % gynoid body fat greater than about 40%; or
   (vii) total body fat greater than about 40 kg.

2. The method of initiating treatment of schizophrenia with brexpiprazole of claim 1, wherein the recommended dose of brexpiprazole is 2 mg/day.

3. The method of initiating treatment of schizophrenia with brexpiprazole of claim 1, wherein the recommended dose of brexpiprazole is 2.25 mg/day.

4. The method of initiating treatment of schizophrenia with brexpiprazole of claim 1, wherein the recommended dose of brexpiprazole is 2.5 mg/day.

5. The method of initiating treatment of schizophrenia with brexpiprazole of claim 1, wherein the recommended dose of brexpiprazole is 2.75 mg/day.

6. The method of initiating treatment of schizophrenia with brexpiprazole of claim 1, wherein the recommended dose of brexpiprazole is 3 mg/day.

7. The method of initiating treatment of schizophrenia with brexpiprazole of claim 1, wherein the recommended dose of brexpiprazole is 3.25 mg/day.

8. The method of initiating treatment of schizophrenia with brexpiprazole of claim 1, wherein the recommended dose of brexpiprazole is 3.5 mg/day.

9. The method of initiating treatment of schizophrenia with brexpiprazole of claim 1, wherein the recommended dose of brexpiprazole is 3.75 mg/day.

10. The method of initiating treatment of schizophrenia with brexpiprazole of claim 1, wherein the recommended dose of brexpiprazole is 4 mg/day.

11. A method of initiating treatment of schizophrenia with brexpiprazole in an obese patient who is a CYP2D6 poor metabolizer, comprising:
    (a) administering 0.5 mg brexpiprazole twice daily on each of the first 4 days of brexpiprazole treatment;
    (b) administering 1 mg brexpiprazole twice daily on each of the next 3 days following step (a); and then
    (c) administering 1-2 mg/day of brexpiprazole once daily thereafter;
wherein the obese patient has one or more of the following characteristics:
    (i) BMI of at least about 35;
    (ii) % IBW of at least about 150%;
    (iii) waist size greater than about 42 inches;
    (iv) % body fat greater than about 40%;
    (v) % android body fat greater than about 40%;
    (vi) % gynoid body fat greater than about 40%; or
    (vii) total body fat greater than about 40 kg.

12. The method of initiating treatment of schizophrenia with brexpiprazole of claim 11, wherein half of the recommended dose of brexpiprazole is 1 mg/day.

13. The method of initiating treatment of schizophrenia with brexpiprazole of claim 11, wherein half of the recommended dose of brexpiprazole is 1.25 mg/day.

14. The method of initiating treatment of schizophrenia with brexpiprazole of claim 11, wherein half of the recommended dose of brexpiprazole is 1.5 mg/day.

15. The method of initiating treatment of schizophrenia with brexpiprazole of claim 11, wherein half of the recommended dose of brexpiprazole is 1.75 mg/day.

16. The method of initiating treatment of schizophrenia with brexpiprazole of claim 11, wherein half of the recommended dose of brexpiprazole is 2 mg/day.

17. A method of initiating adjunctive treatment of major depressive disorder with brexpiprazole in an obese patient who is not a CYP2D6 poor metabolizer, comprising:
    (a) administering either 0.5 or 1 mg brexpiprazole twice daily on each of the first 7 days of brexpiprazole treatment;
    (b) administering double the individual brexpiprazole dose of step (a) once daily on each of the next 7 days following step (a); and then
    (c) administering the recommended daily dose of brexpiprazole once daily thereafter;
wherein the obese patient has one or more of the following characteristics:
    (i) BMI of at least about 35;
    (ii) % IBW of at least about 150%;
    (iii) waist size greater than about 42 inches;
    (iv) % body fat greater than about 40%;
    (v) % android body fat greater than about 40%;
    (vi) % gynoid body fat greater than about 40%; or
    (vii) total body fat greater than about 40 kg.

* * * * *

UNITED STATES PATENT AND TRADEMARK OFFICE
CERTIFICATE OF CORRECTION

PATENT NO. : 11,951,105 B2
APPLICATION NO. : 17/575316
DATED : April 9, 2024
INVENTOR(S) : Sundar Srinivasan et al.

It is certified that error appears in the above-identified patent and that said Letters Patent is hereby corrected as shown below:

In the Claims

Column 44, Claim 12, Line numbers 2-3, "wherein half of the recommended dose of brexpiprazole is" should read -- wherein the dose of brexpiprazole in step (c) is --

Column 44, Claim 13, Line numbers 5-6, "wherein half of the recommended dose of brexpiprazole is" should read -- wherein the dose of brexpiprazole in step (c) is --

Column 44, Claim 14, Line numbers 8-9, "wherein half of the recommended dose of brexpiprazole is" should read -- wherein the dose of brexpiprazole in step (c) is --

Column 44, Claim 15, Line numbers 11-12, "wherein half of the recommended dose of brexpiprazole is" should read -- wherein the dose of brexpiprazole in step (c) is --

Column 44, Claim 16, Line numbers 14-15, "wherein half of the recommended dose of brexpiprazole is" should read -- wherein the dose of brexpiprazole in step (c) is --

Signed and Sealed this
Fourth Day of March, 2025

Coke Morgan Stewart
*Acting Director of the United States Patent and Trademark Office*